United States Patent [19]
Lee et al.

[11] Patent Number: 5,840,013
[45] Date of Patent: Nov. 24, 1998

[54] METHOD OF INTRODUCING A TUBULAR MEMBER AT A SITE IN THE BODY

[76] Inventors: Jai S. Lee, 1205 Clearfield Cir., Lutherville, Md. 21093; InBae Yoon, 2101 Highland Ridge Dr., Phoenix, Md. 21131

[21] Appl. No.: 768,241

[22] Filed: Dec. 17, 1996

Related U.S. Application Data

[62] Division of Ser. No. 214,527, Mar. 18, 1994, Pat. No. 5,645,519.

[51] Int. Cl.$^6$ ........................................................ A61B 1/04
[52] U.S. Cl. .............................................. 600/114; 600/120
[58] Field of Search ....................................... 600/120, 114, 600/115, 116, 184, 188, 190, 194, 201, 235, 237; 128/200.26, 207.14, 207.15, 911, 912

[56] References Cited

U.S. PATENT DOCUMENTS

| | | |
|---|---|---|
| 1,613,373 | 1/1927 | Beck . |
| 1,650,959 | 11/1927 | Pitman . |
| 1,680,491 | 9/1928 | Wappler et al. . |
| 2,022,065 | 11/1935 | Wappler . |
| 2,433,705 | 12/1947 | Palmeter . |
| 2,918,917 | 12/1959 | Emerson . |
| 3,005,452 | 10/1961 | Pitman . |
| 3,091,235 | 5/1963 | Richards . |
| 3,195,536 | 7/1965 | Hovnanian et al. . |
| 3,373,736 | 3/1968 | Fiore et al. . |
| 3,598,113 | 8/1971 | Moore et al. . |
| 3,643,654 | 2/1972 | Felberg . |
| 3,677,262 | 7/1972 | Zukowski . |
| 3,709,214 | 1/1973 | Robertson . |
| 3,726,272 | 4/1973 | Fukami et al. . |
| 3,760,797 | 9/1973 | Stauffer . |
| 3,766,909 | 10/1973 | Ozbey . |
| 3,771,514 | 11/1973 | Huffman et al. . |
| 3,776,222 | 12/1973 | Smiddy . |
| 3,830,225 | 8/1974 | Sbinnick . |
| 3,850,162 | 11/1974 | Iglesias . |
| 3,884,222 | 5/1975 | Moore . |
| 3,913,568 | 10/1975 | Carpenter . |
| 3,916,881 | 11/1975 | Heine . |
| 3,941,120 | 3/1976 | Lee . |
| 3,948,251 | 4/1976 | Hosono . |
| 4,063,561 | 12/1977 | McKenna . |
| 4,085,742 | 4/1978 | Okada . |
| 4,086,919 | 5/1978 | Bullard . |
| 4,122,856 | 10/1978 | Mosior et al. . |
| 4,126,127 | 11/1978 | May . |
| 4,146,019 | 3/1979 | Bass et al. . |
| 4,270,575 | 6/1981 | Reed et al. . |
| 4,319,563 | 3/1982 | Kubota . |
| 4,329,983 | 5/1982 | Fletcher . |
| 4,336,794 | 6/1982 | Ohikama . |
| 4,337,761 | 7/1982 | Upsher . |
| 4,344,419 | 8/1982 | Burgin . |
| 4,402,310 | 9/1983 | Kimura . |
| 4,408,598 | 10/1983 | Ueda . |
| 4,437,458 | 3/1984 | Upsher . |

(List continued on next page.)

*Primary Examiner*—Beverly M. Flanagan

[57] ABSTRACT

An endoscopic instrument for controlled introduction of tubular members in the body includes a blade assembly having a blade for being introduced in the body to retract or manipulate anatomical tissue for introduction of a tubular member at a site in the body, a tubular member assembly having a tubular member with a distal end for being introduced at the site in the body and a remote viewing assembly having a distal end for being positioned in the body to permit introduction of the tubular member at the site in the body to be confirmed visually at a location remote from the site in the body. The distal end of the tubular member and the distal end of the remote viewing device are movable along the blade to introduce the tubular member distal end at the site in the body. A method of introducing a tubular member at a site in the body includes the steps of inserting a blade of an instrument in the body, retracting anatomical tissue with the blade, moving a distal end of a tubular member of the instrument distally along the blade to introduce the distal end of the tubular member at the site in the body and visualizing introduction of the tubular member at the site in the body with a remote viewing device from a location remote from the site in the body.

42 Claims, 14 Drawing Sheets

U.S. PATENT DOCUMENTS

| | | |
|---|---|---|
| 4,517,962 | 5/1985 | Heckele . |
| 4,527,553 | 7/1985 | Upsher . |
| 4,580,556 | 4/1986 | Kondur . |
| 4,592,343 | 6/1986 | Upsher . |
| 4,598,698 | 7/1986 | Siegmund . |
| 4,616,630 | 10/1986 | Arakawa . |
| 4,617,915 | 10/1986 | Arakawa . |
| 4,694,826 | 9/1987 | Chester . |
| 4,742,819 | 5/1988 | George . |
| 4,779,612 | 10/1988 | Kishi . |
| 4,832,020 | 5/1989 | Augustine . |
| 4,838,245 | 6/1989 | Storz . |
| 4,846,153 | 7/1989 | Berci . |
| 4,886,049 | 12/1989 | Darras . |
| 4,905,669 | 3/1990 | Bullard et al. . |
| 4,930,495 | 6/1990 | Upsher . |
| 4,947,829 | 8/1990 | Bullard . |
| 5,003,963 | 4/1991 | Bullard et al. . |
| 5,016,614 | 5/1991 | MacAllister . |
| 5,042,469 | 8/1991 | Augustine . |
| 5,095,888 | 3/1992 | Hawley ................................... 600/194 |
| 5,131,380 | 7/1992 | Heller et al. . |
| 5,152,277 | 10/1992 | Honda et al. . |
| 5,174,283 | 12/1992 | Parker . |
| 5,183,031 | 2/1993 | Rossof . |
| 5,184,603 | 2/1993 | Stone . |
| 5,203,320 | 4/1993 | Augustine . |
| 5,257,620 | 11/1993 | Schermerhorn . |
| 5,257,636 | 11/1993 | White . |
| 5,263,472 | 11/1993 | Ough . |
| 5,263,478 | 11/1993 | Davis . |
| 5,285,778 | 2/1994 | Mackin . |
| 5,287,848 | 2/1994 | Cubb et al. . |
| 5,363,838 | 11/1994 | George ................................... 600/194 |

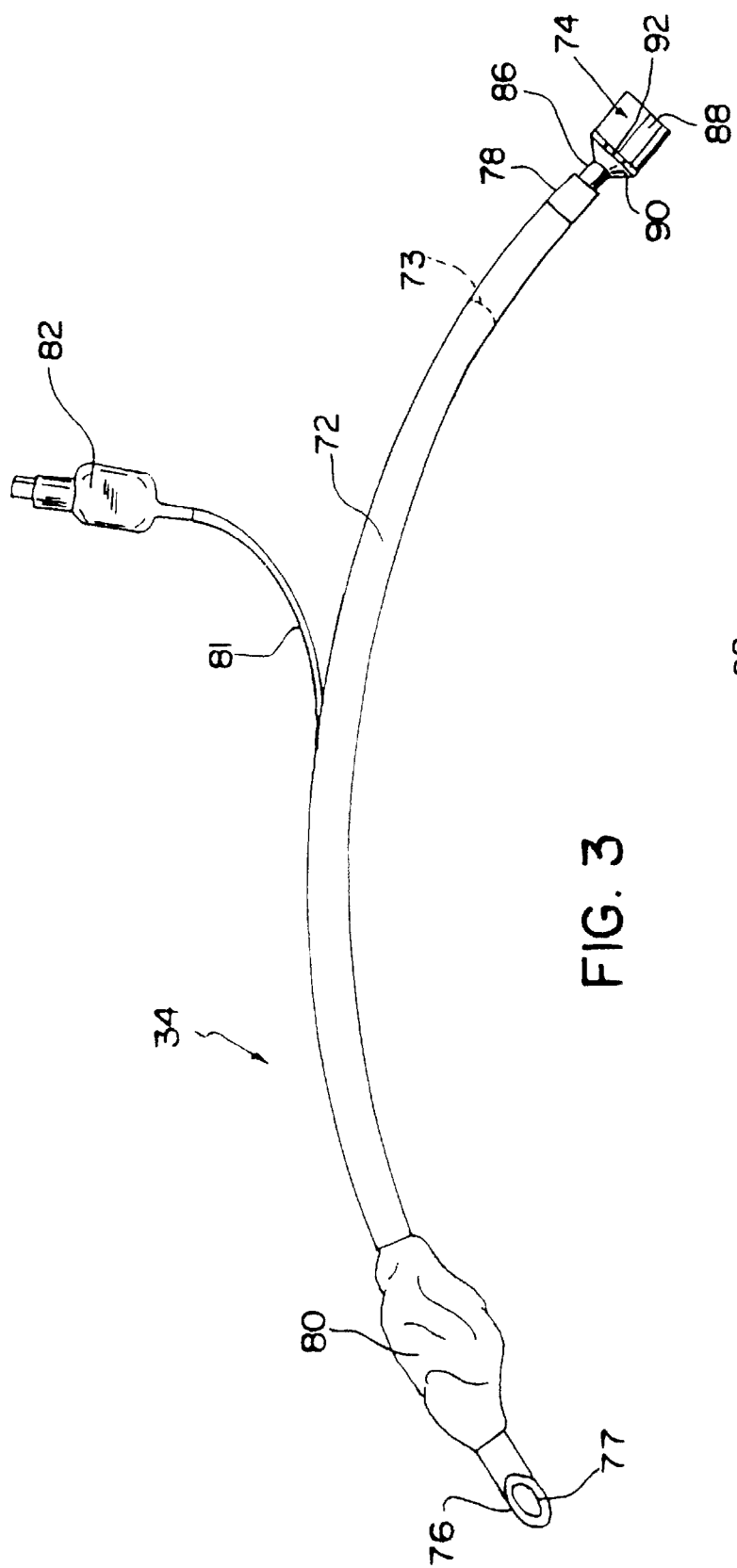
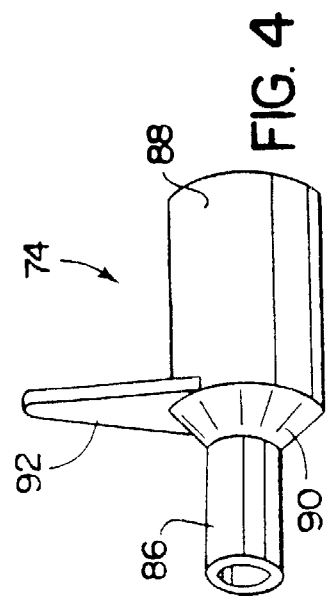
FIG. 3
FIG. 4

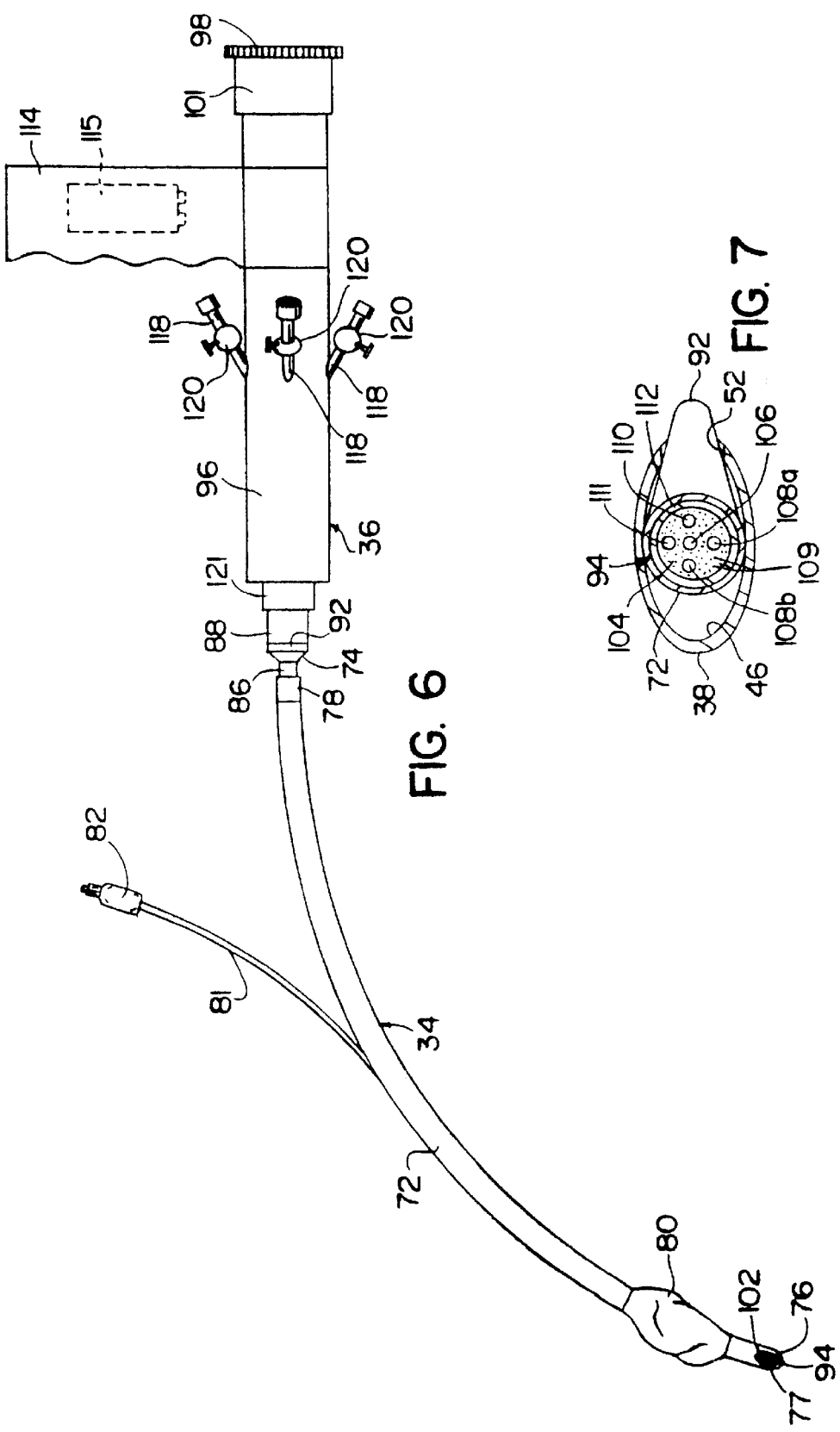

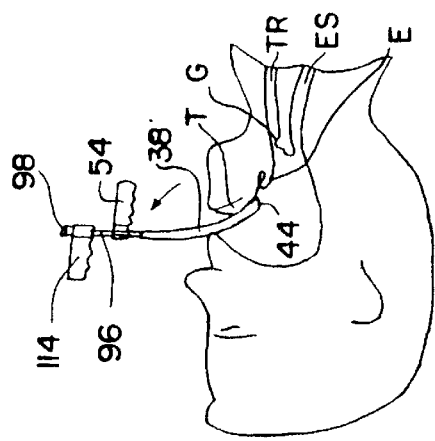
FIG. 8C
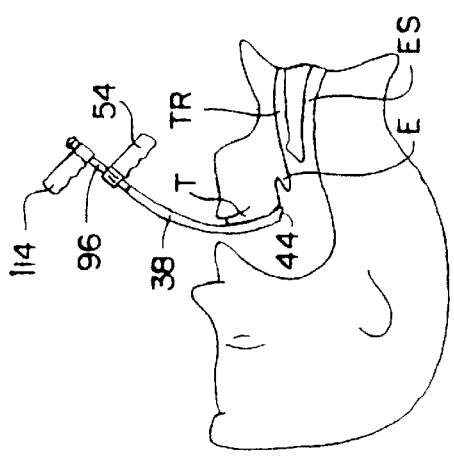
FIG. 8B
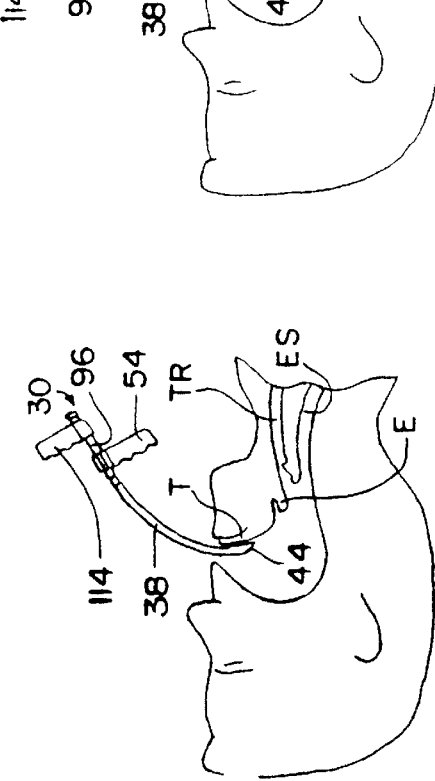
FIG. 8A
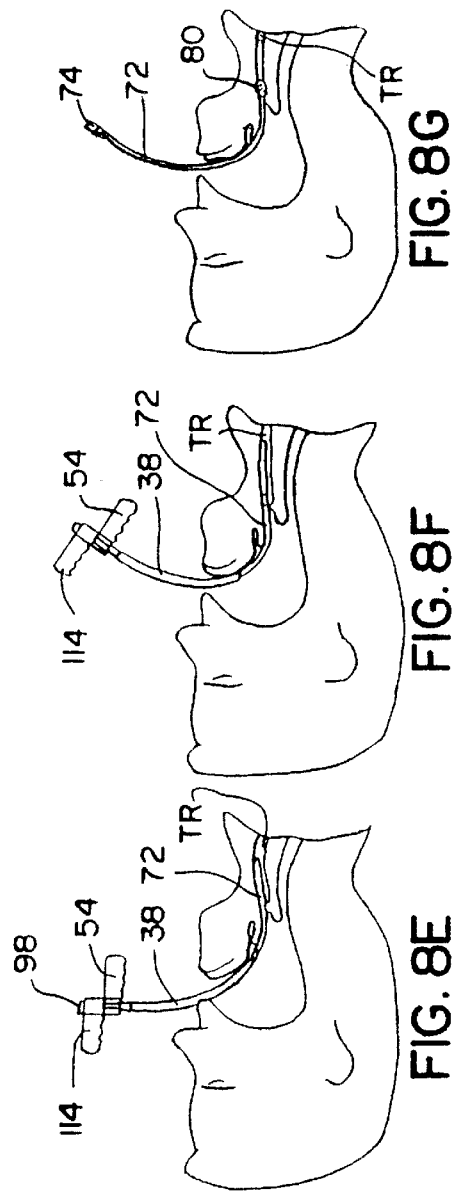
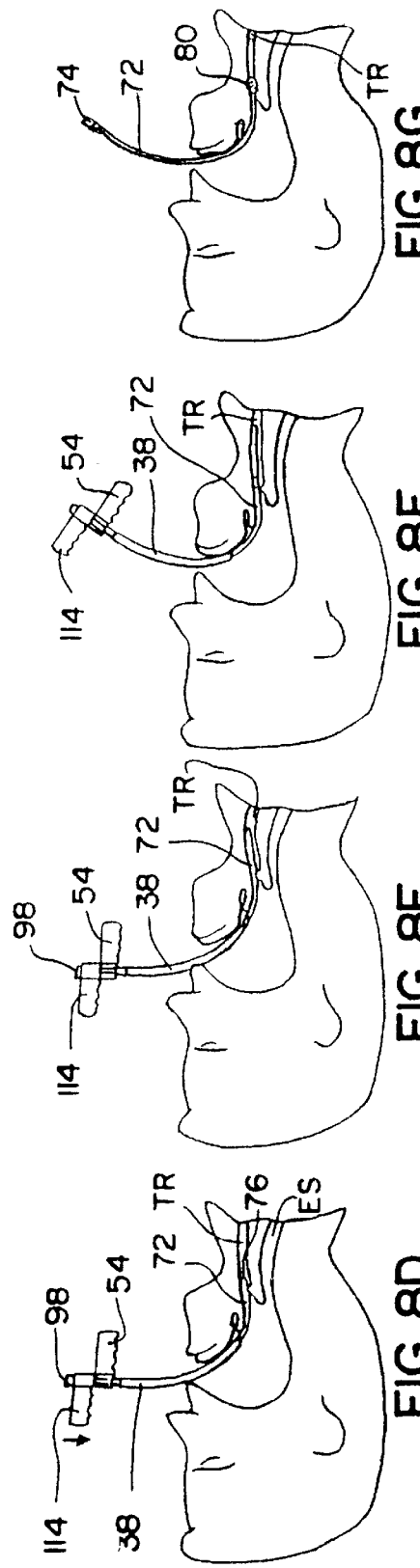

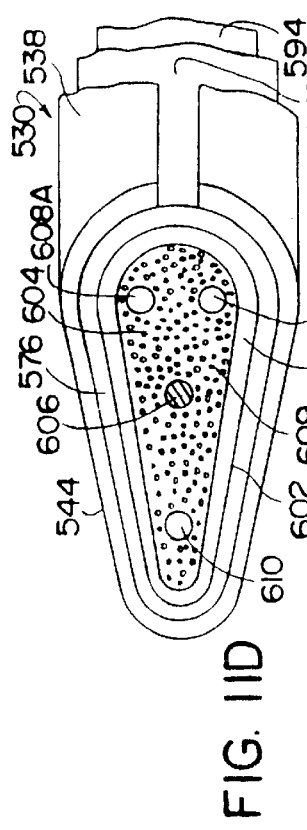
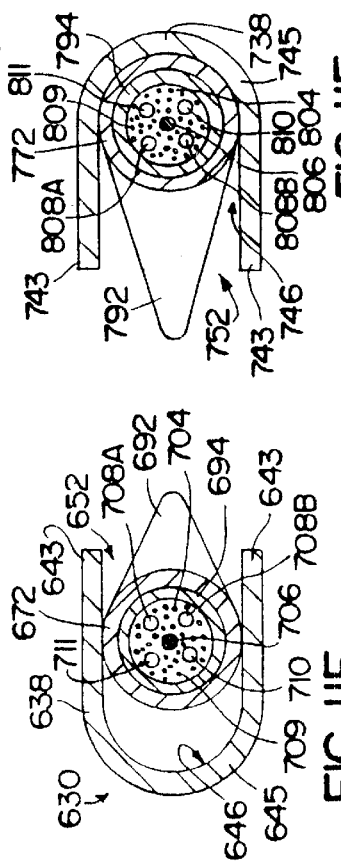
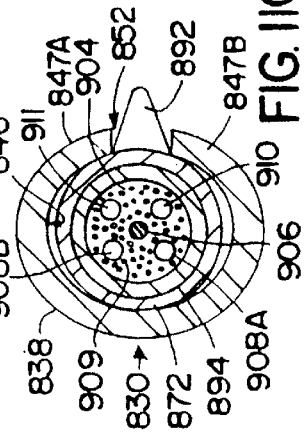
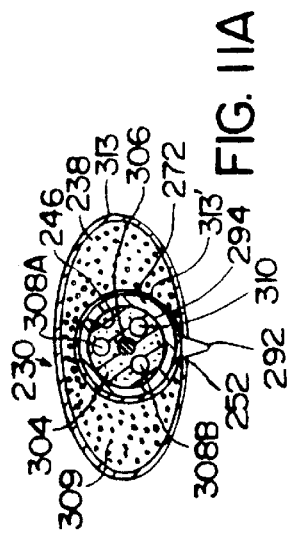
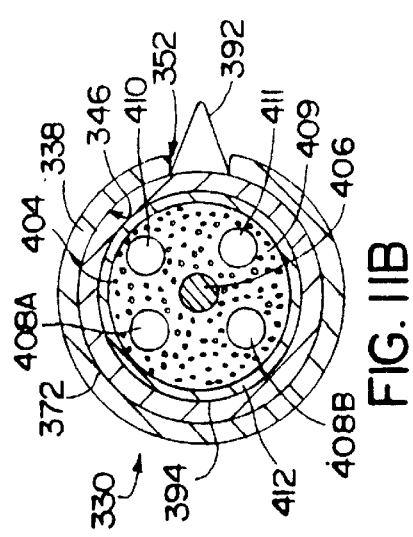
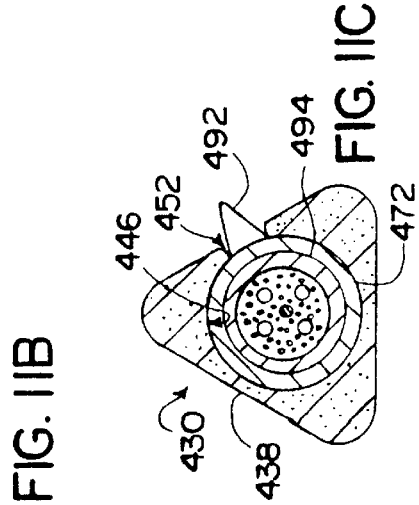

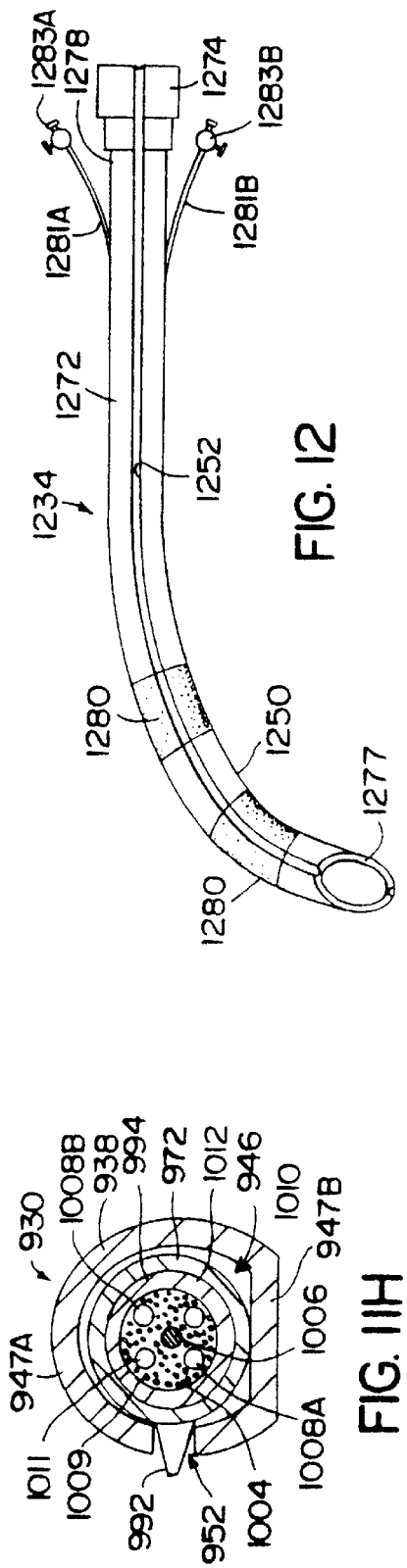
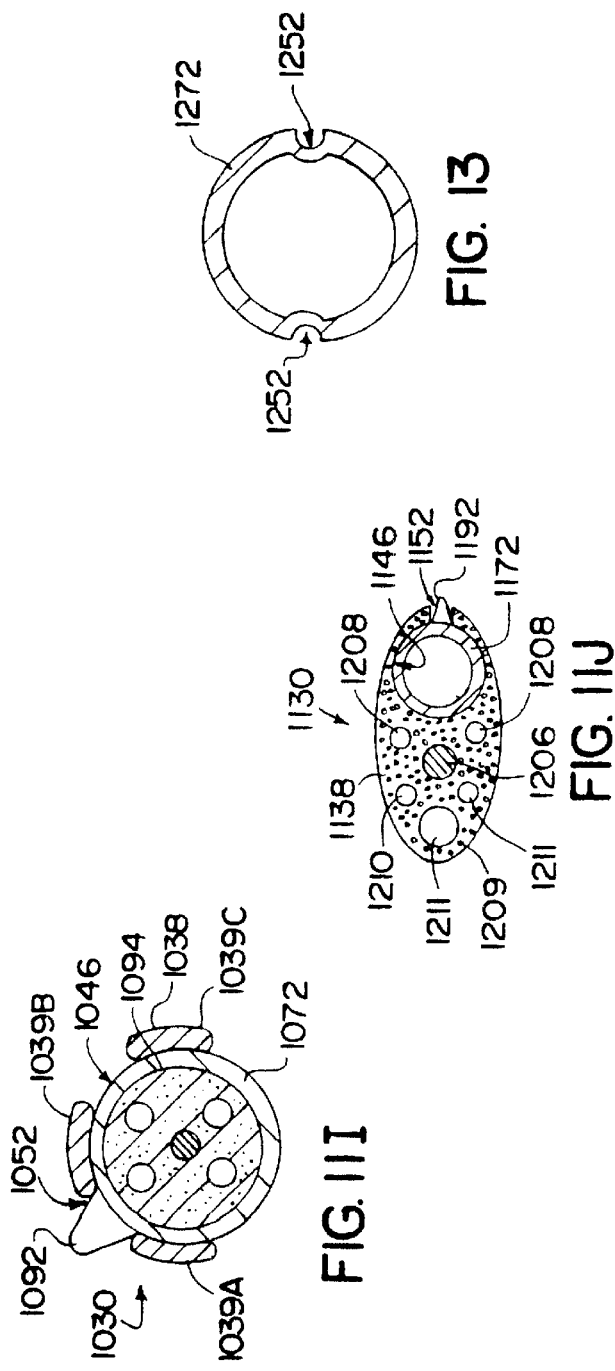

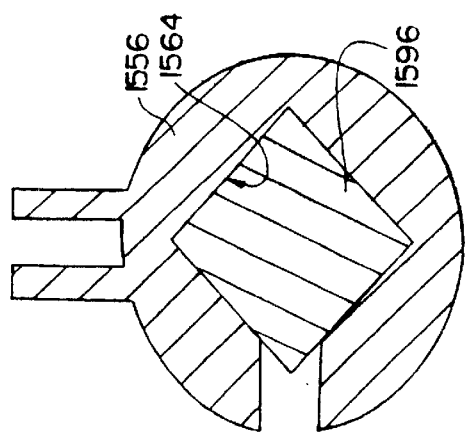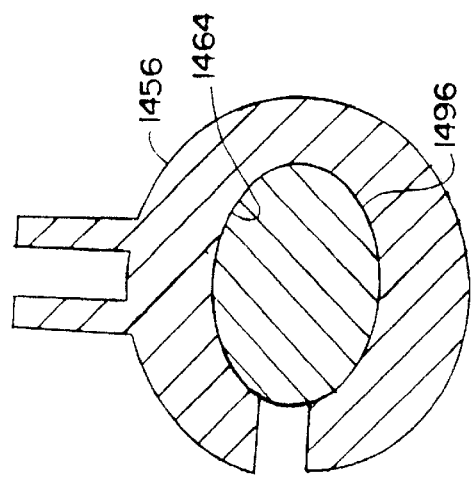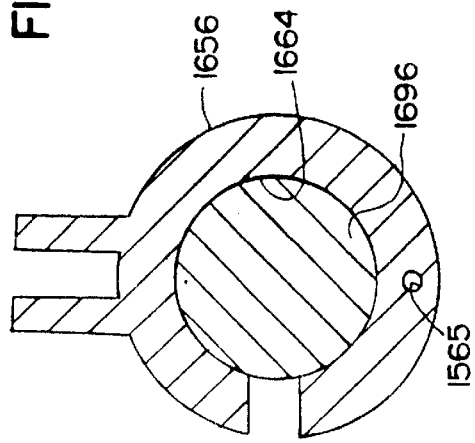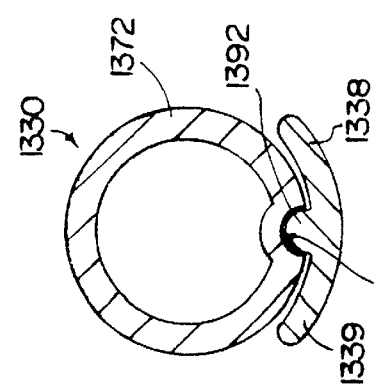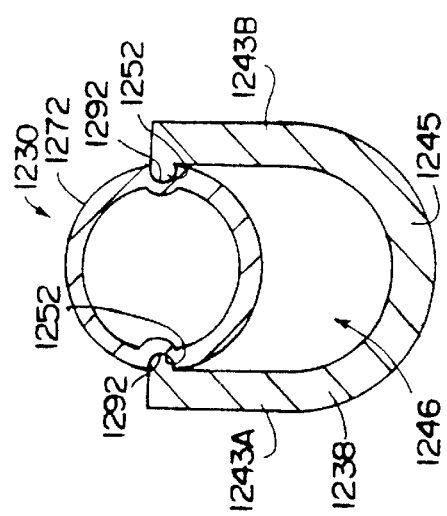

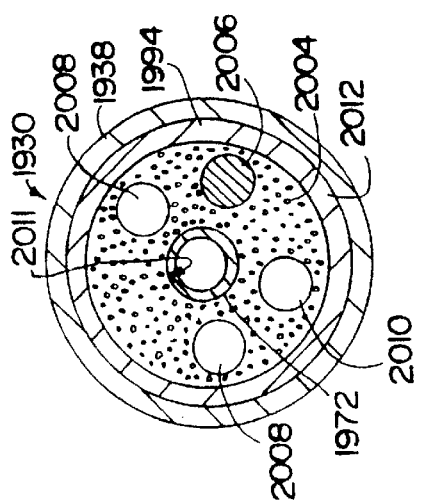
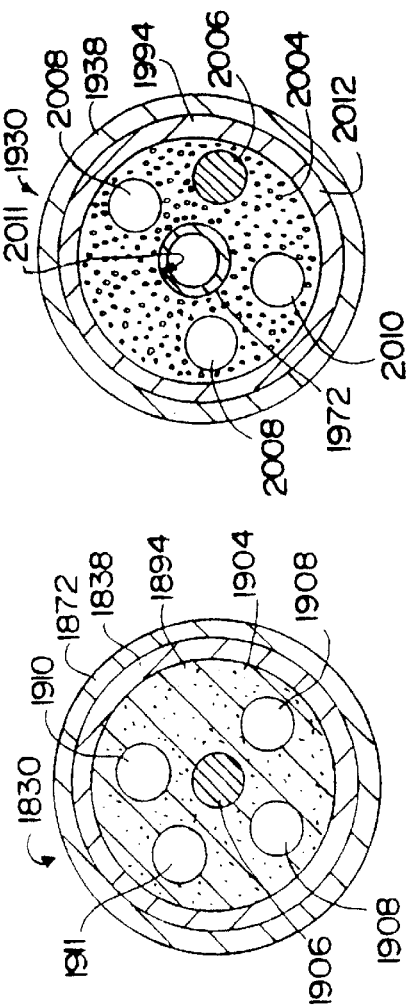
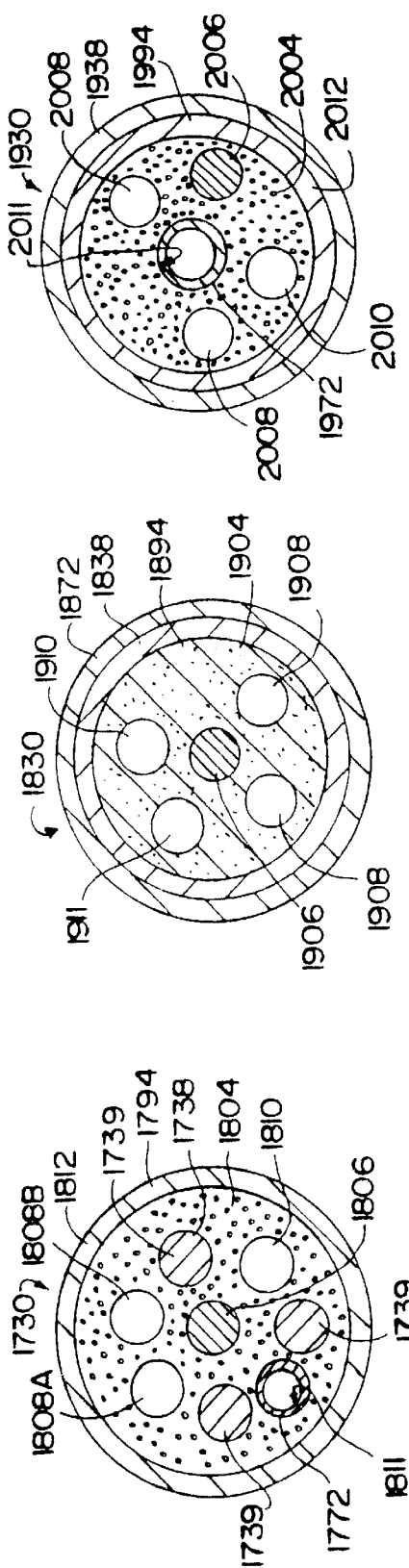
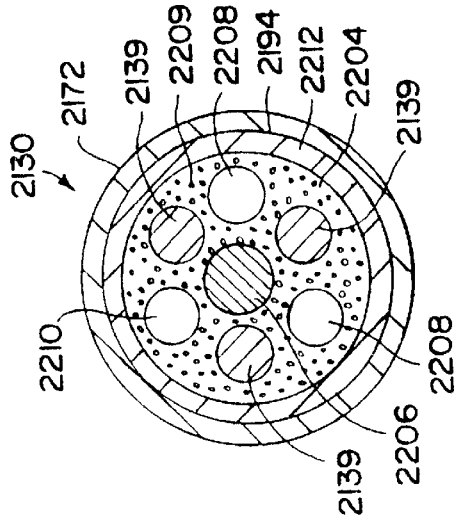
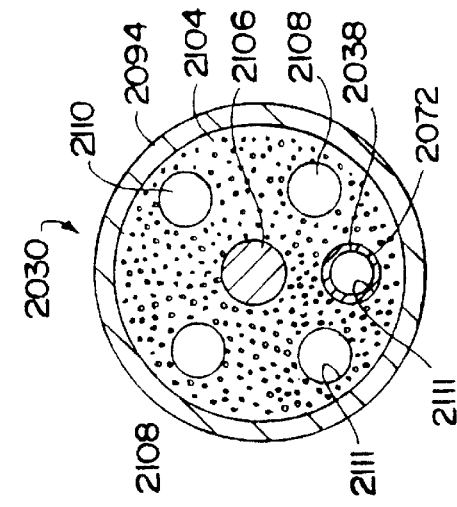

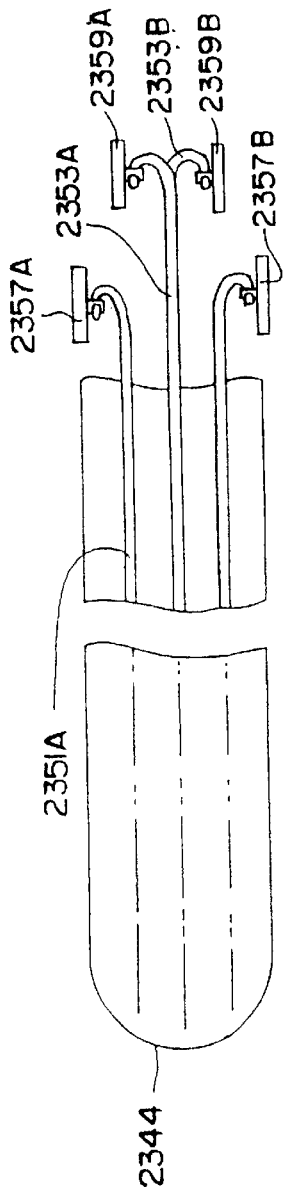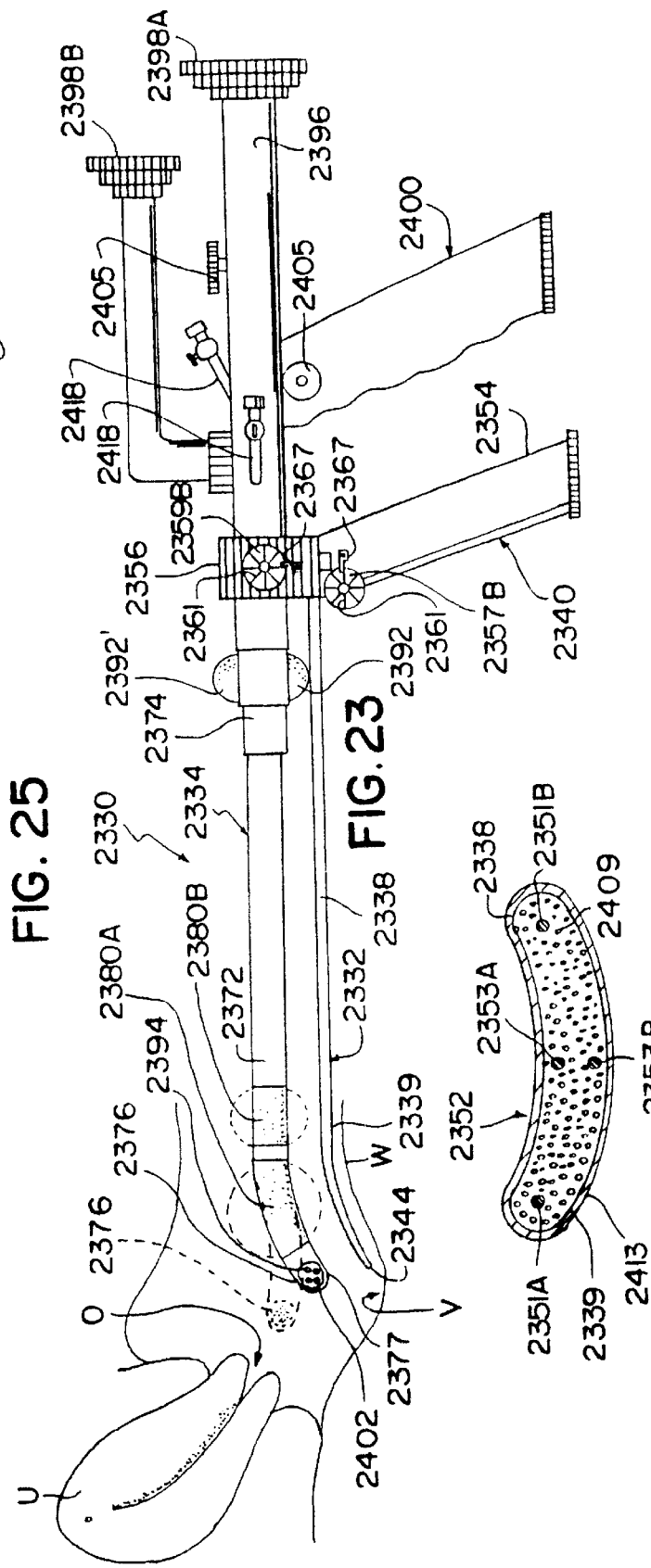

METHOD OF INTRODUCING A TUBULAR MEMBER AT A SITE IN THE BODY

This application is a divisional of prior application Ser. No. 08/214,527 filed Mar. 18, 1994, the disclosure of which is incorporated herein by reference.

BACKGROUND OF THE INVENTION

1. Field of the Invention

The present invention relates generally to endoscopic instruments and, more particularly, to endoscopic instruments for controlled introduction of tubular members in the body and to methods therefor.

2. Description of the Prior Art

Various medical procedures require the introduction of tubular members, such as endotracheal tubes, catheters and cannulas, in the body of a patient. Frequently, distal ends of the tubular members are required to be positioned at sites in the body, including natural or artificial openings or channels in the body, from remote locations that do not permit direct access to and/or observation of the sites in the body. Lack of direct access and/or visibility makes it difficult to accurately position the distal ends of the tubular members at the designated sites from the remote locations, particularly where the tubular members are flexible to conform to the contours of anatomical structure. Depending on the medical procedures being performed, improper positioning of the tubular members can result in various adverse consequences for the patient.

The safety and efficacy of procedures for introducing tubular members in the body can be greatly enhanced with the use of remote or endoscopic visualization wherein a distal end of an endoscope is introduced in the body to permit visualization of the procedures via an eyepiece of the endoscope optically coupled with the image receiving distal end. Introduction of tubular members with the assistance of remote visualization is highly desirable for many various medical procedures; however, even with the assistance of remote visualization, many medical procedures involving introduction of tubular members remain difficult to perform and carry a risk of adverse consequences for the patient. In particular, it is difficult when introducing tubular members in the body to obtain accurate, clear exposure of sites in the body such as body channels or canals in which and/or through which the tubular members are introduced, to introduce the tubular members without trauma or injury to anatomical tissue and to visually inspect or examine the sites in the body. One medical procedure that is difficult to perform even with remote visualization and that is potentially dangerous for patients is endotracheal intubation.

Endotracheal intubation is a frequently utilized, important way to obtain adequate ventilation or respiration in a patient in many circumstances where spontaneous breathing is compromised. In endotracheal intubation, a flexible endotracheal tube is positioned in the patient's trachea or windpipe via the nose, or more commonly, the mouth, to establish a secured airway allowing ventilation or respiration of the patient in various situations including trauma, coma, cardiac arrest, drug-induced depression, acute or chronic pulmonary diseases causing breathing difficulties, cardiopulmonary resuscitation, seizures, respirator care and general anesthesia. With a distal end of the endotracheal tube positioned in the trachea, a proximal end of the endotracheal tube can be coupled with a source of gas or drugs, such as a respirator for supplying oxygen, to permit gas or drugs to be delivered to the lungs via the endotracheal tube.

There are many reasons why endotracheal intubation is difficult to perform and potentially dangerous for the patient. One reason is that the anatomical oropharyngeal passage, i.e. the passage of the mouth and upper throat, is curved and narrow making it difficult for a physician, nurse, anesthetist or other trained medical professional to view and properly guide the distal end of the endotracheal tube into the trachea. Another reason is that the epiglottis normally overlies the glottis opening to the larynx at the upper end of the trachea to prevent the passage of food into the trachea during eating, and the epiglottis must be moved during endotracheal intubation to expose the glottis. A further reason is that, once the glottis is exposed, the endotracheal tube must be accurately passed through the glottis, between the vocal cords and into the trachea, and not inadvertently into the esophagus which is adjacent the trachea and separated therefrom by the corniculus. Yet another reason is that endotracheal intubation must be performed quickly because brain damage and even death of the patient can occur in a matter of several minutes. Exposure of the glottis and introduction of the endotracheal tube in the trachea is very difficult and stressful to perform, even for highly trained medical personnel. When not performed properly, endotracheal intubation can have many adverse consequences for the patient including injury to the front incisors, damage to oropharyngeal, laryngopharyngeal and other tissue, hypoxia, brain damage and death.

Various instruments, such as laryngoscopes, have been proposed to facilitate and improve the safety and efficacy of endotracheal intubation. Such laryngoscopes typically include an endoscope and a blade for manipulating anatomical tissue to expose the glottis. During straightforward or normal endotracheal intubations as typically performed with a laryngoscope, the patient is placed in a supine position on a support surface with the neck fully extended, and the blade is inserted into the patient's mouth to position a distal end or tip of the blade at the base of the tongue. The blade is used to apply gentle upward pressure at the base of the tongue to move the tongue and epiglottis anteriorly to expose the glottis, which is viewed remotely via an eyepiece of the endoscope. With the glottis exposed, the endotracheal tube is advanced along side the blade through the glottis, between the vocal cords and into the trachea. The laryngoscope is then withdrawn leaving the endotracheal tube in the body, and a cuff at a distal end of the endotracheal tube is inflated to secure the endotracheal tube in place in the trachea.

Although straightforward endotracheal intubations with laryngoscopic assistance can be successfully and safely performed in most patients, the procedure remains difficult and stressful to perform even for medical personnel with considerable skill and expertise. Since individual oropharyngeal channels vary greatly among patients in size, shape, and distensibility, significant skill and experience are required to properly position or angle the laryngoscopes and to advance the endotracheal tubes. Additionally, visualization is often impaired by secretions such as blood or vomitus, by anatomical structure or by structure of the conventional laryngoscopes themselves such that the glottis may not be clearly visible even with the assistance of the laryngoscopes. Furthermore, prior art laryngoscopes for endotracheal intubation have many disadvantages in that the endotracheal tubes cannot be advanced in a controlled manner relative to the blades, the endoscopes cannot be advanced in a controlled manner relative to the blades and/or cannot be introduced in the trachea to confirm proper intubation, the distal ends of the endotracheal tubes and/or endoscopes cannot be accurately controlled or guided, the distal ends of the endoscopes cannot be optimally positioned to view the glottis, the components of the instruments are arranged in a manner requiring considerable space such that visualization is obstructed by the instruments themselves and the instruments cause trauma to anatomical tissue, manipulation of the instruments commonly results in damage to oropharyngeal, laryngopharyngeal and other tissue, the instruments are complex and not suitable for use by lesser skilled medical personnel or in emergency situations, the distances that the endotracheal tubes are advanced in the trachea cannot be accurately gauged, operation of the laryngoscopes requires complex maneuvers by both hands of the operator, the head of the patient must be tilted back very far such that neck and spinal injuries can result or be aggravated, the instruments are not suitable for use in what are known as difficult endotracheal intubations and the instruments are not suitable for use in bronchial intubation.

Although straightforward or normal endotracheal intubation is in general difficult to perform and has potential adverse consequences for the patient, there are six particular patient types in which endotracheal intubation is excessively difficult to perform and dangerous for the patient. These patient types include patients having (1) a large tongue relative to the size of the pharynx; (2) poor mobility of the mandible or limited ability to tilt back the head sufficiently, i.e., limited atlantooccipital joint extension; (3) a short muscular neck and a full set of teeth; (4) a receding mandible with obtuse or narrow mandibular angles; (5) a long, arched palate associated with a long, narrow mouth; and, (6) large or protruding incisors and relative maxillary overgrowth or anteriorly located larynx, i.e., a small anterior mandibular space. For the latter patient types, visualization of the glottis is particularly impaired or not possible even with the assistance of remote visualization such that there is an increased risk that the endotracheal tube will be inadvertently placed in the esophagus which can result in hypoxia, brain damage or death due to suffocation. Additionally, rotating or angling conventional laryngoscopes in an effort to visualize and/or expose the glottis in difficult intubations commonly results in injury to the teeth and/or to oropharyngeal and laryngopharyngeal tissue. Since it has been estimated that 20% of endotracheal intubations can be characterized as difficult, a significant problem is presented. This problem is compounded in that most difficult endotracheal intubations are not anticipated but, rather, are identified as difficult after failure to achieve intubation with conventional laryngoscopes such that there is usually little time available before serious consequences will occur.

Various approaches and procedures have been proposed for dealing with unanticipated difficult endotracheal intubations including nasal fiber optic intubation, retrograde intubation, blind nasal intubation, flexible bronchoscopy, tracheostomy and intubation with specialized laryngoscopes. In addition to the disadvantages previously discussed for conventional laryngoscopes and straightforward endotracheal intubation, the foregoing approaches have various additional drawbacks including bleeding, trauma, the need for specialized skill, the need for preparation and implementation time which may be in excess of the time available to prevent brain damage or death of the patient, the need to switch to instruments with which the operator is less familiar, the need for instruments that are complex in structure and use and increased stress for medical personnel performing unanticipated difficult endotracheal intubations. Various other medical procedures and instruments for introducing tubular members in the body share the same drawbacks and disadvantages as straightforward and difficult endotracheal intubations.

SUMMARY OF THE INVENTION

Accordingly, it is a primary object of the present invention to overcome the aforementioned disadvantages of prior art endoscopic instruments for introducing tubular members in the body.

Another object of the present invention is to provide a single endoscopic instrument for introducing endotracheal tubes in straightforward as well as difficult endotracheal intubations whereby the problem of unanticipated difficult endotracheal intubations can be eliminated or minimized.

It is also an object of the present invention to provide a single endoscopic instrument for controlled non-traumatic introduction of tubular members at various sites in the body for various medical procedures such as endotracheal intubation, esophagoscopy, bronchoscopy, proctoscopy, vaginoscopy, hysteroscopy, colposcopy, rectosigmoidoscopy, laparoscopy, subcutaneoscopy, mammascopy and inflatable endoscopic procedures in the cardiovascular, gastrointestinal and neuromuscular systems.

An additional object of the present invention is to provide an endoscopic instrument for controlled introduction of tubular members in the body having a blade for manipulating anatomical tissue to facilitate introduction of the tubular members with the blade having a predetermined shape or being adjustable along a length of the blade to optimally manipulate the tissue.

A further object of the present invention is to provide an endoscopic instrument for controlled introduction of tubular members in the body including a blade assembly, a remote viewing assembly and a tubular member assembly with a tubular member of the tubular member assembly being adjustable along a length of the tubular member.

A still further object of the present invention is to provide an endoscopic instrument for controlled introduction of tubular members in the body having a blade for guiding introduction of the tubular members with the blade being adjustable to assume and maintain a predetermined shape or being adjustable along a length of the blade to optimally manipulate or retract tissue and guide the tubular members.

Yet another object of the present invention is to provide an endoscopic instrument for controlled introduction of tubular members in the body including a blade having structure cooperating with corresponding structure of a remote viewing device to form a track system for controlled movement of the remote viewing device along the blade.

The present invention has as a further object to provide an endoscopic instrument for controlled introduction of tubular members in the body including a blade having structure cooperating with corresponding structure of a tubular member to form a guide system for controlled movement of the tubular member along the blade.

Still a further object of the present invention is to provide an endoscopic instrument for controlled introduction of tubular members in the body wherein a tubular member and a remote viewing device are movable distally relative to a blade, and the tubular member is movable further distally relative to the blade and the remote viewing device.

Another object of the present invention is to provide an endoscopic instrument for controlled introduction of tubular members in the body having a blade, a remote viewing device and a tubular member assembled to form an instrument assembly having a smooth periphery to prevent trauma to anatomical tissue when the instrument assembly is introduced in the body.

Yet another object of the present invention is to provide an endoscopic instrument for controlled introduction of tubular members in the body including a blade, a remote viewing device and a tubular member concentrically arranged with one another.

The present invention has as a further object to provide an endoscopic instrument for controlled introduction of tubular members in the body wherein a tubular member and a remote viewing device are movable longitudinally, separately or in conjunction, in a controlled manner relative to a blade.

An additional object of the present invention is to provide an endoscopic instrument for controlled introduction of tubular members in the body including a blade for guiding introduction of a tubular member in the body and means for gauging the distance or depth that the tubular member is introduced in the body.

It is also an object of the present invention to provide a method of endotracheal intubation with an instrument for introducing an endotracheal tube in the trachea including the steps of moving a distal end of an endotracheal tube of the instrument and a distal end of a remote viewing device of the instrument distally along a blade of the instrument and into the trachea and visualizing the trachea with an eyepiece of the remote viewing device.

Another object of the present invention is to provide a method of introducing a tubular member at a site in the body including moving a tubular member of an instrument and a remote viewing device of the instrument distally along a blade of the instrument toward the site in the body and guiding distal movement of the remote viewing device along the blade.

A still further object of the present invention is to provide a method of bronchial intubation utilizing an instrument for introducing an endotracheal tube in the trachea.

Some of the advantages of the present invention are that the safety and efficacy of procedures for introducing tubular members in the body are greatly enhanced, tubular members can be introduced at sites in the body with clear, accurate exposure of the sites in the body as well as. body channels in which or through which the tubular members are introduced, sites in the body can be inspected incident to the introduction of the tubular members, the safety and efficacy of both straightforward and difficult endotracheal intubations are greatly enhanced, both straightforward and difficult endotracheal intubations are greatly simplified, endotracheal intubations can be performed in accordance with the present invention by medical personnel having various levels of skill, adverse consequences due to improper endotracheal intubation are avoided, proper endotracheal intubation can be visually confirmed by observing the anatomical characteristics of the trachea, improper endotracheal intubation can be visually identified by observing the anatomical characteristics of the esophagus allowing immediate correction, the instruments according to the present invention occupy minimal space for introduction in narrow anatomical channels or openings, for enhanced visualization and for elimination or reduction in trauma to anatomical tissue, the instruments according to the present invention permit various advantageous arrangements of the blade assembly, the tubular member assembly and the remote viewing assembly, the components of the instruments are functional separately, the instruments can be used to introduce tubular members in any anatomical cavity, passage or canal as well as natural or artificial anatomical openings, and bronchial intubation can be performed with the same instrument utilized for endotracheal intubation and without the need for a separate bronchoscope.

These and other objects, advantages and benefits are realized with the present invention as characterized in an instrument for controlled introduction of tubular members in the body including a blade assembly, a tubular member assembly and a remote viewing assembly. The blade assembly includes a blade having a distal end for being positioned in the body to manipulate or retract tissue to permit introduction of a tubular member of the tubular member assembly at the site in the body. The tubular member includes a distal end for being introduced at the site in the body and is movable, individually or in conjunction with the remote viewing device, relative to the blade to introduce the tubular member distal end at the site in the body. The remote viewing assembly includes a remote viewing device movable, individually or in conjunction with the tubular member, relative to the blade to position a distal end of the remote viewing device in the body to permit introduction of the tubular member at the site in the body to be visualized via an eyepiece of the remote viewing device remote from the site in the body. A track system of the instrument guides movement of the remote viewing device relative to the blade, and a guide system of the instrument guides movement of the tubular member relative to the blade.

The present invention is further characterized in a method of introducing a tubular member, such as an endotracheal tube, at a site in the body, such as the trachea, comprising the steps of moving a tubular member and a remote viewing device of an instrument along a blade of an instrument toward the site in the body, guiding movement of the remote viewing device along the blade, introducing a distal end of the tubular member at the site in the body and visualizing introduction of the tubular member at the site in the body with an eyepiece of the remote viewing device remote from the site in the body.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 3 is a side view of the tubular member assembly of the instrument of FIG. 1.

FIG. 4 is a side view of the adapter of the tubular member assembly of FIG. 3.

FIG. 6 is a side view of the remote viewing assembly of FIG. 5 assembled with the tubular member assembly of FIG. 3.

FIG. 7 is a cross-sectional view of the instrument of FIG. 1.

FIGS. 8A–8G progressively illustrate a method of endotracheal intubation utilizing the instrument of FIG. 1.

FIGS. 11A–11J are cross-sectional views of further embodiments of the instrument according to the present invention utilizing various modified blade assemblies.

FIG. 12 is a side view of a modification of the tubular member assembly for the instrument according to the present invention.

FIG. 13 is a cross-sectional view of the tubular member assembly of FIG. 12.

FIG. 14 is a cross-sectional view of an additional embodiment of the instrument according to the present invention utilizing the tubular member assembly of FIG. 12.

FIG. 15 is a cross-sectional view of another embodiment of the instrument according to the present invention.

FIGS. 16A–16C are cross-sectional views of modifications of the track system for the instrument of the present invention.

FIGS. 17–21 are cross-sectional views of additional embodiments of the instrument according to the present invention illustrating various alternative arrangements for the blade assembly, the tubular member assembly and the remote viewing assembly.

FIG. 23 is a side view of another embodiment of an instrument according to the present invention showing the instrument in use in a procedure to introduce a tubular member in the uterus.

FIG. 24 is an enlarged cross-sectional view of the blade for the instrument of FIG. 23.

FIG. 25 is a top schematic view of the blade assembly for the instrument of FIG. 23.

DESCRIPTION OF THE PREFERRED EMBODIMENTS

Figure 1:
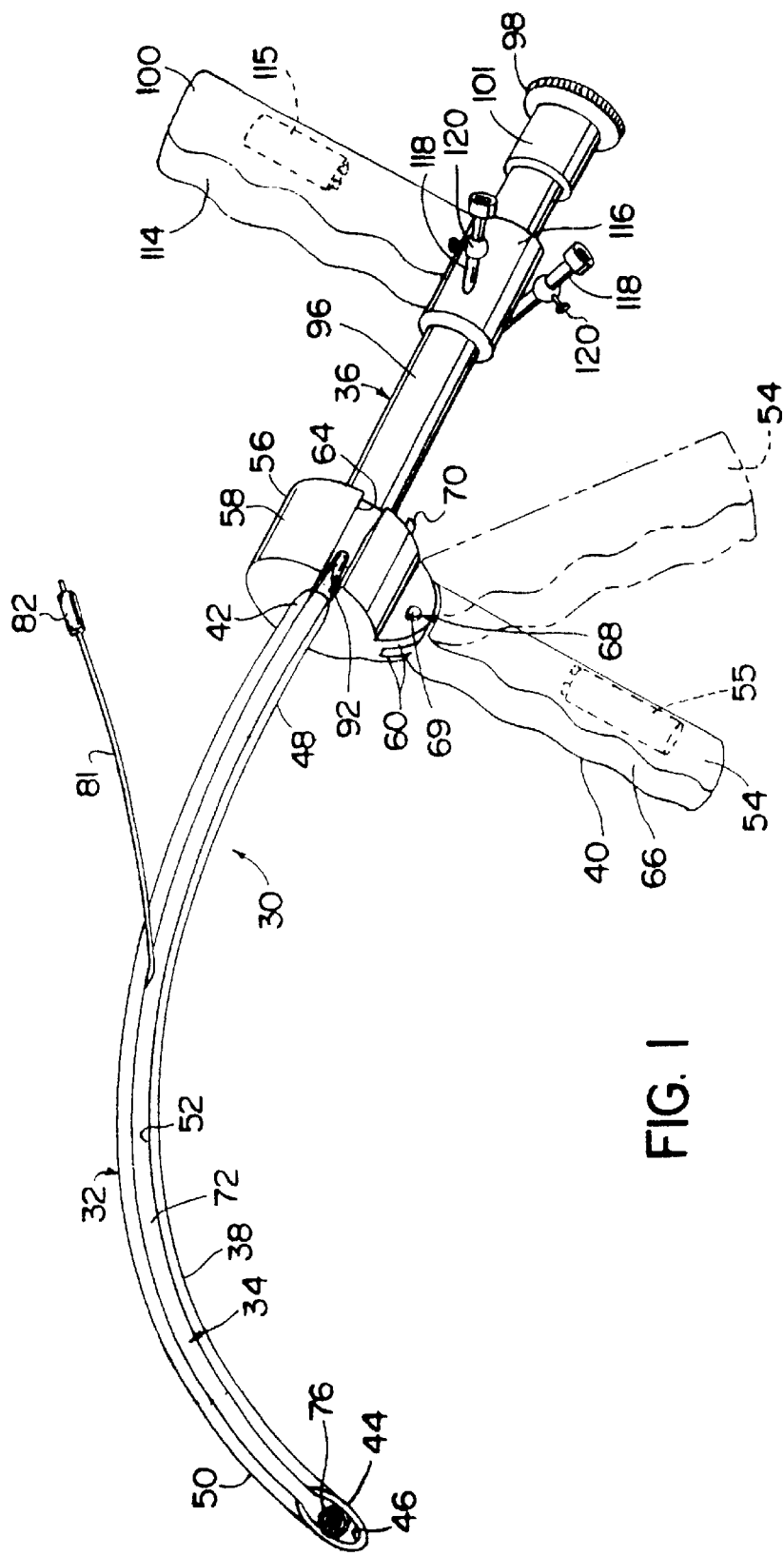
FIG. 1 is a perspective view of an endoscopic instrument for introduction of tubular members in the body according to the present invention.

An endoscopic instrument 30 for controlled introduction of tubular members in the body according to the present invention is illustrated in FIG. 1 and includes a blade assembly 32, a tubular member assembly 34 and a remote viewing assembly 36. Blade assembly 32 is made up of a blade 38 and a blade handle 40 mounting blade 38. Blade 38 includes an elongate blade body terminating proximally at a proximal end 42 and distally at a distal end 44 with a lumen or passage 46 between the distal and proximal blade ends. Blade 38 can be made of any desirable rigid or semi-rigid, semi-flexible or bendable medical grade materials, including metals or plastics, as well as light transmitting materials as shown in FIG. 11C, and can include a plurality of optical fibers as shown in FIG. 11A. The blade can be sterilizable for reuse or disposable for single patient use depending on the materials and structure of the blade.

Figure 2:
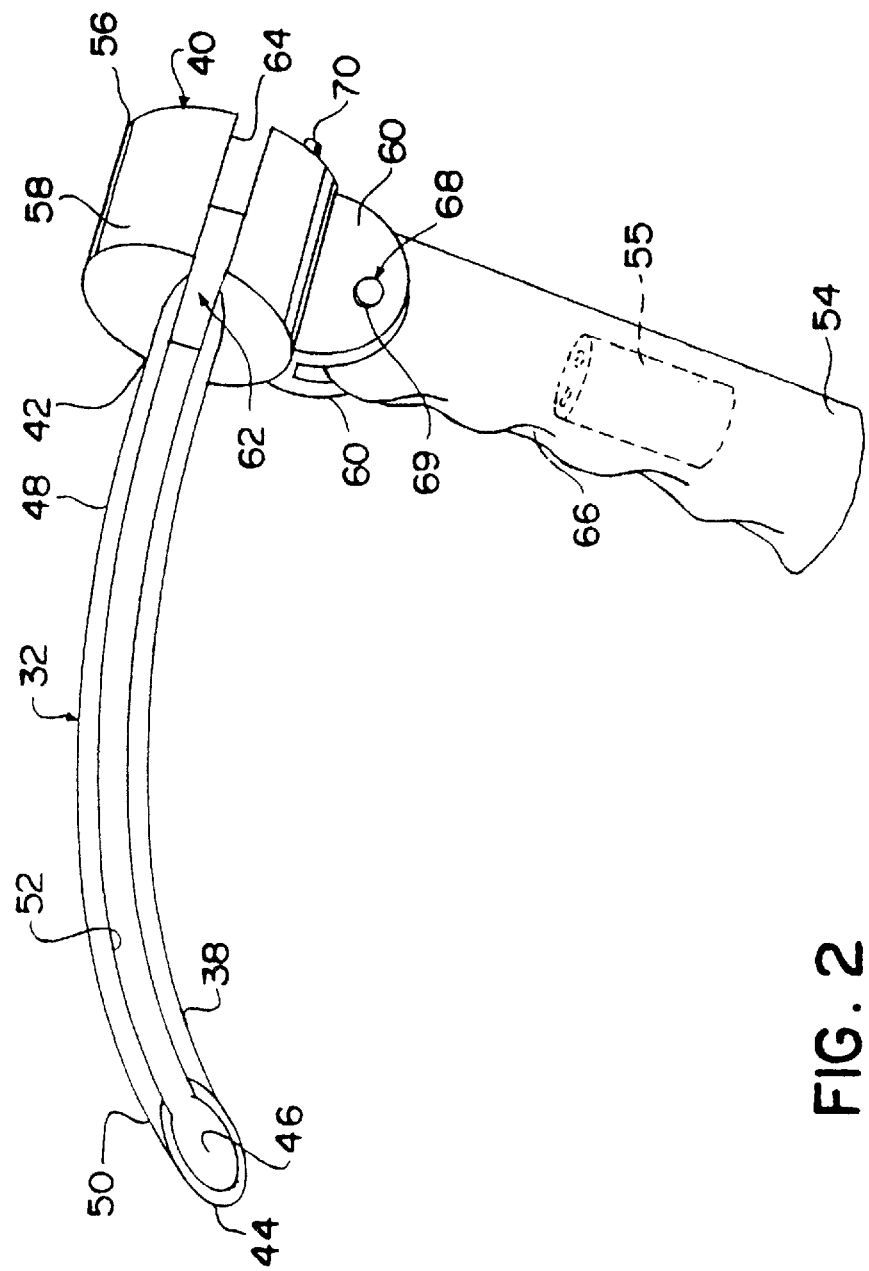
FIG. 2 is a broken perspective view of the blade assembly of the instrument of FIG. 1.

Blade 38 has a configuration along a length of the blade dependent on procedural use. As shown in FIGS. 1 and 2, blade 38 is particularly useful for endotracheal intubation and has a straight or substantially straight proximal segment 48 and a curved distal segment 50 joined to proximal segment 48 such that the configuration of the blade in a longitudinal or lengthwise direction corresponds to the anatomical oropharyngeal curve; however, either or both of the proximal and distal segments can be straight or curved depending upon procedural use. By making the blade 38 of bendable material, the configuration of the blade in the longitudinal direction can be adjusted to assume a shape in accordance with procedural use and/or the particular anatomical characteristics of a patient. Where the blade is made of a bendable material for adjustability, it is desirable that the material of the blade be rigid enough to maintain the shape of the blade during use. One material suitable for construction of an adjustable blade is thermoplastic. It will be appreciated that the blade can be partly rigid or fixed and partly adjustable such as by making the blade partly of a bendable material and partly of a non-bendable material such that, for example, proximal segment 48 can be rigid and distal segment 50 can be bendable or adjustable. The curvature of blade 38 can be made adjustable in various other ways including a series of wires connected from the distal end 44 to wire tightening mechanisms at proximal end 42 for controlling and maintaining the curvature or shape of the blade as shown in FIG. 23 or by making the blade of jointed sections with miniaturized motors and gears for positioning the jointed sections at various angles. The length of the blade can be made adjustable in various ways including making the blade of telescoping sections and providing expansion joints along the length of the blade. Where the blade includes a plurality of optical fibers, the fibers can be arranged in passage 46 or within the walls of the blade.

Blade 38 can have any desirable configuration in cross-section, such as circular, semi or partial circular, oval, elliptical, C-shaped, crescent shaped, triangular, U-shaped and single or multi-pronged configurations, depending on procedural use, and one or more than one blade can be provided in the instrument 30. As shown in FIGS. 1 and 2, blade 38 has an elliptical or oval cross-sectional configuration to facilitate introduction of the blade in the oropharyngeal passage and traction with the tongue as explained further below. Passage 46 has a configuration in cross-section to receive a tube, cannula or catheter of the tubular member assembly 34; and, as shown, passage 46 has an oval cross-sectional configuration. The blade 38 can be made in many various ways, such as from a length of solid material having passage 46 machined therein, from a flat strip or piece of material bent or shaped to define passage 46, by the arrangement of one or more prongs or by molding. Blade 38 defines a longitudinal guide channel 52 for cooperating with a guide protrusion of tubular member assembly 34 to form a guide system for guiding movement of the tubular member assembly along the blade 38. As shown in FIGS. 1 and 2, guide channel 52 takes the form of a longitudinal slot disposed in blade 38 in communication with passage 46, the slot extending distally from proximal end 42 to distal end 44. Channel 52 can be a recess or slot or a protrusion and can be formed in blade 38 in many various ways depending on the structure of the blade. For example, where the channel is a slot, the channel can be formed by cutting out a portion of a wall of the blade, leaving a gap or space between edges or sides of a strip or piece of material bent to form the blade, by a molded configuration of the blade or by the arrangement of one or more prongs of the blade. The blade distal end 44 can be made of a soft or rubbery material, such as silicone rubber, to prevent injury to anatomical tissue and can have various configurations depending on procedural use. As shown, the distal end 44 has a blunt configuration to prevent damage to anatomical tissue or organ structure.

Blade handle 40 includes a hand grip 54 and a collar 56 coupling blade 38 with hand grip 54. Collar 56 can be made of any desirable medical grade materials, including metals and plastics, to be disposable or sterilizable for reuse, and the materials of the collar and the blade can be the same or different. Collar 56 can have any desirable configuration or structure to couple blade 38 with hand grip 54 and to define a track for guiding longitudinal movement of remote viewing assembly 36. As shown in FIGS. 1 and 2, collar 56 is made up of a cylindrical sleeve 58 and a pair of spaced, parallel mounting flanges 60 extending from sleeve 58. Sleeve 58 has an internal passage therethrough of an oval or elliptical cross-sectional configuration corresponding to but larger in size than the cross-sectional configuration of blade 38; however, the sleeve 58 can have any other desirable configuration in cross-section. Flanges 60 have a planar, semi-circular shape and extend outwardly from the sleeve 58 in a direction perpendicular or transverse to a longitudinal axis of the sleeve. The sleeve 58 and the flanges 60 can be made integrally, unitarily as a single piece or component or separately as multiple pieces or components, and the collar 56 can be made integrally, unitarily with or separately from the blade 38. Where the collar and the blade are made as separate components, the proximal end 42 of the blade can be removably or releasably attached to the collar, such as with a friction fit, threads, locking pins or other detent mechanisms.

Collar 56 includes a track 62 for cooperating with structure of the remote viewing assembly 36 to form a track system for guiding or controlling longitudinal movement of the remote viewing assembly. As shown in FIG. 2, track 62 is formed of a longitudinal track channel in sleeve 58 aligned or continuous with passage 46 of blade 38. Track channel 62 has a configuration in cross-section corresponding to the configuration of structure of remote viewing assembly 36 to form a monorail track system with the remote viewing assembly as explained further below. A guide channel 64 continuous with guide channel 52 is defined by collar 56 and is formed of a longitudinal slot 64 in the sleeve 58 aligned or continuous with slot 52 of blade 38.

Hand grip 54 can be made of any suitable materials and can have any desired configuration to facilitate grasping by an operator with one hand. As shown in FIG. 2, hand grip 54 has an elongate, cylindrical configuration with distally facing finger indentations 66 along the length thereof to facilitate grasping by the operator. An end of hand grip 54 is received between flanges 60 with a connector 68 securing the hand grip to the collar 56. Connector 68 can have any suitable construction to couple the hand grip with the collar; and, as shown, connector 68 is in the nature of a swivel lock joint including a pin, joint or hinge 69 pivotally mounting the hand grip 54 to the flanges 60 and a locking and releasing button 70 for locking the hand grip relative to the collar and for releasing the hand grip for rotational or pivotal movement relative to the collar around pin 69, the hand grip 54 being shown in FIG. 1 locked at substantially a right angle to straight proximal segment 48 of blade 38. In many instances, the optimal position for hand grip 54 will be other than a right angle position, one preferred position for the hand grip in endotracheal intubation being shown in dotted lines in FIG. 1 where the hand grip is at an angle of approximately 45° with the proximal segment 48. Where the blade is made of light transmitting material or includes a plurality of optical fibers, a battery 55, as shown in dotted lines in FIG. 1, can be disposed in hand grip 54 for powering a light source (not shown) to transmit light via the blade to the distal end thereof.

Tubular member assembly 34, as best shown in FIG. 3, includes an elongate tube, cannula or catheter 72 and an adapter or connector 74 mounted to tube 72. The tube 72 can be made of any desirable medical grade materials, such as plastics, and can have any desirable configuration in cross-section depending on procedural use. As shown in FIG. 3, the tube 72 is in the nature of an endotracheal tube made of flexible plastic and having a distal end 76 with an angled or beveled end surface 77, a proximal end 78 mounted to the adapter 74 and a lumen between the distal and proximal ends of the tube. A cuff 80 in the nature of a distensible or inflatable floppy bag or balloon is disposed adjacent the distal end 76 for distention or inflation with fluids such as air via a cuff distension device including a cuff distension tube 81 coupled with a cuff distension connector 82. The endotracheal tube 72 illustrated in FIG. 3 can be conventional such that the instrument 30 can be utilized with conventional endotracheal tubes typically having an inside diameter in the range of 5 mm–9 mm and does not require specialized endotracheal tubes. The tube 72 can be modified in accordance with the present invention by forming the tube 72 with a non-circular periphery and/or with an external protrusion 73, shown in dotted lines in FIG. 3. The protrusion 73 can have any desired shape to register with slot 52; and, as shown, the protrusion 72 has a somewhat triangular or conical shape.

Adapter 74, as shown in FIG. 4, includes a tubular forward end 86, a tubular rearward end 88 longitudinally aligned with forward end 86, a sloping intermediate section 90 joining the forward and rearward ends and a guide tab or protrusion 92 for cooperating with guide channel 52 of blade 38. Forward end 86 has an external cross-sectional configuration to be received in the lumen of tube 72 with a friction fit when the adapter 74 is assembled with tube 72. Rearward end 88 has an external cross-sectional configuration corresponding to but larger in size than the external cross-sectional configuration of the forward end 86, with intermediate section 90 having a truncated conical configuration. Guide tab 92 is joined to the rearward end 88 adjacent intermediate section 90 and extends outwardly therefrom in a direction radial or transverse to a longitudinal axis of the adapter 74. As shown in FIG. 3, the guide tab 92 is arranged on the same side of tube 72 as the angled surface 77 and is in alignment with the angled surface to optimally position the angled surface for passage between the vocal cords and to provide an indicator function relating to the position of the distal end of the tube. It will be appreciated, however, that the adapter can be arranged on the tube with the guide tab offset from the angled surface to change the orientation of the angled surface when the tubular member assembly is assembled with the blade assembly. The guide tab 92 is tapered in the direction outwardly from the rearward section to define a triangular or pie-shaped configuration; however, the guide tab can have various other desirable configurations to be conveniently grasped and to cooperate with guide channel 52 of blade 38 for guiding movement of tube 72. The triangular configured guide tab 92 shown for instrument 30 has sloping sides for engaging opposing sides of channel 52 to prevent rotation and/or lateral movement of tube 72 relative to blade 38 and for controlled distal movement of tube 72 relative to blade 38 as will be explained further below.

Figure 5:
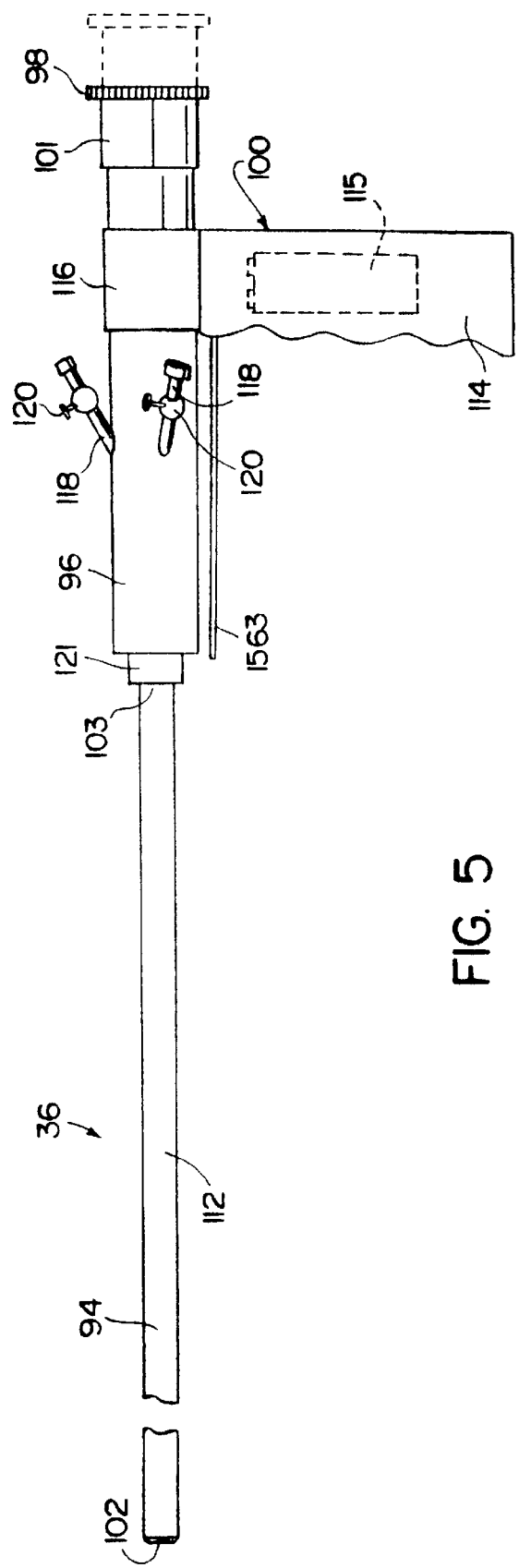
FIG. 5 is a broken side view of the remote viewing assembly of the instrument of FIG. 1.
Figure 10:
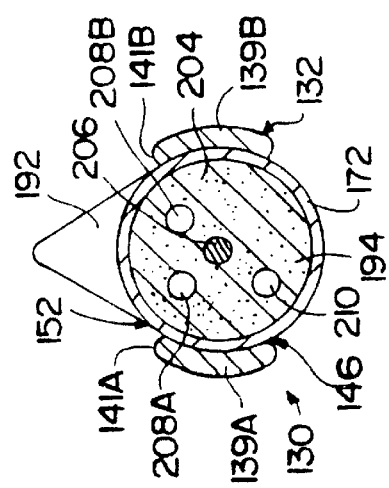
FIG. 10 is a cross-sectional view of an alternative embodiment of the instrument according to the present invention utilizing the blade assembly of FIG. 9.

Remote viewing assembly 36, as shown in FIG. 5, is in the nature of an endoscope including an elongate probe 94, a control section 96 mounting a proximal end of the probe 94, an eyepiece 98 mounted to control section 96 and a handle 100. Probe 94 includes a distal end 102 for introduction in the body and a proximal end 103 mounted to control section 96. Within or forming probe 94 are a light transmitting channel 104, an image transmitting channel 106 and one or more delivery channels 108 as shown in FIG. 7. Light transmitting channel 104 communicates with a light source to transmit light from the light source to illuminate an area from the probe distal end 102. The light transmitting channel 104 can be formed as a plurality of optical fibers 109 as shown in FIG. 7 or by a single length of light transmitting material as shown in FIG. 10. The image transmitting channel 106 transmits an image at distal end 102 for visualization through the eyepiece 98. The image transmitting channel 106 is preferably centrally arranged in probe 94 and includes a plurality of optical fibers extending between the eyepiece 98 and the probe distal end 102 and/or one or more lenses or image transmitters for transmitting an image at the probe distal end 102 to the eyepiece 98. The light transmitting and image transmitting channels can be separate channels as shown in FIG. 7 or a single channel. The channels 108 include a channel 108a for supplying gas, such as oxygen, through the endoscope, and a channel 108b for supplying medicinal substances, including various drugs, through the endoscope. Probe 94 also includes a suction or ventilation channel 110 for removing blood and other secretions and an operating or working channel 111 through which various instruments can be introduced. The probe 94 can be provided with an outer sheath 112 as shown in FIGS. 5 and 7, with channels 104, 106, 108, 110 and 111 within the sheath 112, or without the sheath 112 as shown in FIG. 10. It will be appreciated that other means can be utilized to form the remote viewing assembly to provide illumination and to transmit an image to eyepiece 98 or to a monitor including rod/lens systems, fiber optic lens systems and photosensor systems wherein a photosensor at a distal end of the probe transmits an image to a television monitor.

The endoscope handle 100 is similar to blade handle 40 and includes a hand grip 114, similar to hand grip 54, and a collar or sleeve 116 receiving the control section 96 of the endoscope with the hand grip 114 extending from collar 116 in a direction perpendicular or transverse to a longitudinal axis of the endoscope. A battery 115 is disposed in hand grip 114 for powering a light source (not shown), with light from the light source being transmitted by fibers 109, as shown in FIG. 7, to the probe distal end 102 to illuminate an area in the body. Control section 96 can be mounted to collar 116 to permit longitudinal movement of the collar 116 along the control section 96 to adjust the position of hand grip 114 and can be detachable or removable from the control section. One or more of the channels 108, 110 and 111 can be connected with or formed by conduits 118 extending through the collar 116 of the endoscope handle and having valves 120, such as stopcocks, for controlling opening and closing of the conduits as shown in FIG. 1, or the conduits can extend through probe 94 and not the collar as shown in FIG. 5. Any number of conduits can be provided, two conduits being shown in FIG. 1 and three conduits being shown in FIG. 6.

The endoscope can be rigid, flexible, partially rigid or partially flexible or adjustable and can include a charge coupled device. The eyepiece 98 can include a high powered eyepiece with or without magnification or microscopic power; and, where magnification is provided, it is desirable that the magnification be in the range of ten to twenty times normal size. It will be appreciated that both regular and magnified views can be provided via separate eyepieces or via a single high powered eyepiece, such as by providing a system of interchangeable lenses movable in and out of alignment with a viewing port of the eyepiece, and the eyepiece can be rotatable and/or longitudinally movable in a telescoping manner. As shown in FIG. 1, eyepiece 98 is mounted via a sleeve 101 for longitudinal movement along control section 96 in the manner of a zoom lens to obtain a magnified image and is rotatable for focusing. The eyepiece 98 can be connected with an adapter for transmitting the image to a television monitor. With the use of a charge coupled device, images obtained with the endoscope can be transmitted to a monitor for viewing and/or videographic recordation. Hand grip 114 can be rotatable as previously described for hand grip 54, and the endoscope handle 100 can be removably or detachably mounted on the control section 96 with a friction fit or with suitable detent mechanisms and can be slidable along the control section. Depending on procedural use, the endoscope handle 100 need not be provided, and the remote viewing device can be held via the control section. One endoscope suitable for use in the instrument 30 is the Olympus flexible endoscope.

Operation of instrument 30 in endotracheal intubation will now be described. The blade assembly 32, the tubular member assembly 34 and the remote viewing assembly 36 are assembled as shown in FIG. 1. The proximal end 78 of the endotracheal tube 72 is placed over the forward end 86 of the adapter 74 to be held thereon with a friction fit with tab 92 aligned with the angled surface 77 as shown in FIG. 3. The probe 94 is inserted in the tube 72 via the rearward end 88 of the adapter 74 until the rearward end 88 is in abutment with control section 96 or a forward nose 121 of the control section 96 as shown in FIG. 6 at which time the angled distal surface 77 will be aligned or substantially aligned with the probe distal end 102. The endotracheal tube 72 with the endoscope probe 94 therein is inserted in blade 38 via track channel 62 and passage 46 with hand grip 114 of the endoscope extending in a direction opposite the blade hand grip 54 as shown in FIG. 1 until the distal ends of the tube and probe are substantially aligned or aligned with the distal end 44 of the blade 38 with tab 92 protruding through guide channel 52. With the instrument assembled as shown in FIG. 1, the control section 96 of the endoscope will be disposed at a proximal end of track channel 62 of collar 56, the control section being maintained at the proximal end of the track channel by a friction fit. The angled surface 77, as shown in FIG. 3, will be facing a side of the instrument 30 with hand grip 54 pointing down and hand grip 114 pointing up. The blade 38, the tube 72 and the probe 94 form an instrument assembly having a periphery or shape that is smooth or rounded and without sharp corners or irregularities to prevent injury or trauma to anatomical tissue and organ structure when the instrument assembly is introduced in the body. Additionally, the instrument assembly occupies minimal space to facilitate passage through narrow anatomical passages such as the oropharyngeal area and to enhance visualization. Alignment of the distal ends of the blade, the tube and the probe forms a smooth distal end shape or surface preventing trauma to anatomical tissue. The blade assembly 32, the tubular member assembly 34 and the remote viewing assembly 36 for instrument 30 are concentrically arranged with one another; and, as shown in FIG. 7, tube 72 will be within blade 38 and probe 94 will be within tube 72.

The instrument 30 is now ready to be utilized to introduce the endotracheal tube 72 into the trachea of a patient as illustrated in FIGS. 8A–8G. According to a method of operation for instrument 30 in endotracheal intubation, the patient is placed in a supine position on a support surface and the distal end 44 of the blade 38 is inserted vertically downwardly into the patient's mouth by an operator grasping the hand grip 54 of the blade assembly 32 as shown in FIG. 8A. The instrument 30 is advanced along the oropharyngeal curve until the distal end 44 of the blade 38 reaches the base of the patient's tongue T as shown in FIG. 8B. As shown in FIG. 8C, once the distal end 44 of the blade 38 has been positioned at the base of the tongue T, the hand grip 54 is pulled slightly upwardly or anteriorly causing the blade 38 in engagement with the tongue to apply anterior pressure or force on the tongue to move the hyoid bone anteriorly which tensions the hyo-epiglottic ligament and elevates the epiglottis E anteriorly to expose the glottis G and vocal cords. Anterior pressure on the tongue is facilitated by traction of blade 38 with the tongue due to the oval configuration of blade 38 minimizing or preventing lateral or rolling movements of the tongue. Once the epiglottis has been moved anteriorly, the exposed glottis and vocal cords are visualized through the eyepiece 98 of the endoscope with the centrally arranged image transmitting channel 106 facilitating visualization. Upon visualization of the glottis and vocal cords through the eyepiece 98, the endotracheal tube 72 and probe 94 are advanced together relative to the blade 38 by pushing the hand grip 114 of the endoscope forwardly to cause the control section 96 of the endoscope to move or slide forwardly or distally along the track channel 62 with the blade 38 maintaining exposure of the glottis and vocal cords as shown in FIG. 8D. Movement of hand grip 114 forwardly or distally, i.e. toward hand grip 54, causes probe 94 and tube 72 to be moved together distally approximately 5 centimeters as controlled by movement of control section 96 along track channel 62 with the control section and the track channel forming a monorail track system guiding or controlling movement of the remote viewing device and, therefore, the tube 72. Movement of the distal ends of tube 72 and probe 94 distally approximately 5 centimeters causes the distal ends of the tube and the probe to pass through the glottis and between the vocal cords to be introduced in the trachea TR a distance of approximately 5 centimeters, as shown in FIG. 8D, as visualized at eyepiece 98 by observing the anatomical characteristics of the trachea. If the tube has been inadvertently introduced in the esophagus ES, observation of the anatomical characteristics of the esophagus at the eyepiece will immediately alert the operator, and the probe and tube can be quickly withdrawn from the esophagus ES and introduced in the trachea TR, the track system and guide system allowing backing out of the tube and probe. Where advancement of the tube distal end 76 with probe 94 is not sufficient to introduce the distal end of the tube in the trachea or is insufficient to introduce the tube a desired depth or distance in the trachea, the guide tab 92 is grasped, and the tube 72 is moved further distally relative to the blade 38 and the probe 94, as controlled by the guide system, to introduce the tube distal end the desired depth or distance in the trachea as shown in FIG. 8E. With the guide tab protruding from a side of the instrument 30, the blade handle can be grasped with one hand, for example the left hand, while the tube is moved by grasping the guide tab with the other hand, for example the right hand, allowing simple use of the instrument in a manner familiar to medical personnel. Introduction of tube 72 in the trachea is confirmed visually via eyepiece 98, and the depth or distance of insertion of tube 72 in the trachea can be gauged by noting the distance that the guide tab 92 has been moved along the guide channel 52. The delivery channels 108 allow gasses, such as oxygen, and drugs to be supplied during or subsequent to the intubation procedure, and the suction channel 110 allows secretions to be aspirated to facilitate visualization. Where other instruments are required to be introduced in the body, the other instruments can be introduced through the working channel 111. Where magnification at eyepiece 98 is provided, anatomical tissue and organ structure can be examined under magnification for early detection or diagnosis of abnormalities or diseases such as cancer. Once tube 72 is properly positioned in the trachea, the blade assembly 32 and the remote viewing assembly 36 are withdrawn from the tubular member assembly 34, as permitted by guide channels 52 and 64, leaving the tube 72 in place as shown in FIG. 8F. Cuff 80 is distended or inflated via the cuff distension device to hold tube 72 in place in the trachea as illustrated in FIG. 8G. Although the tube 72 has been described as being moved in conjunction with the probe 94 when the control section 96 is moved along the track channel 62, the probe 94 can be moved individually by holding the tube 72 stationary via guide tab 92 when the control section 96 is advanced along the track channel. Accordingly, the instrument 30 permits selective distal movement relative to blade 38 of tube 72 alone, probe 94 alone or the tube and the probe together.

Figure 9:
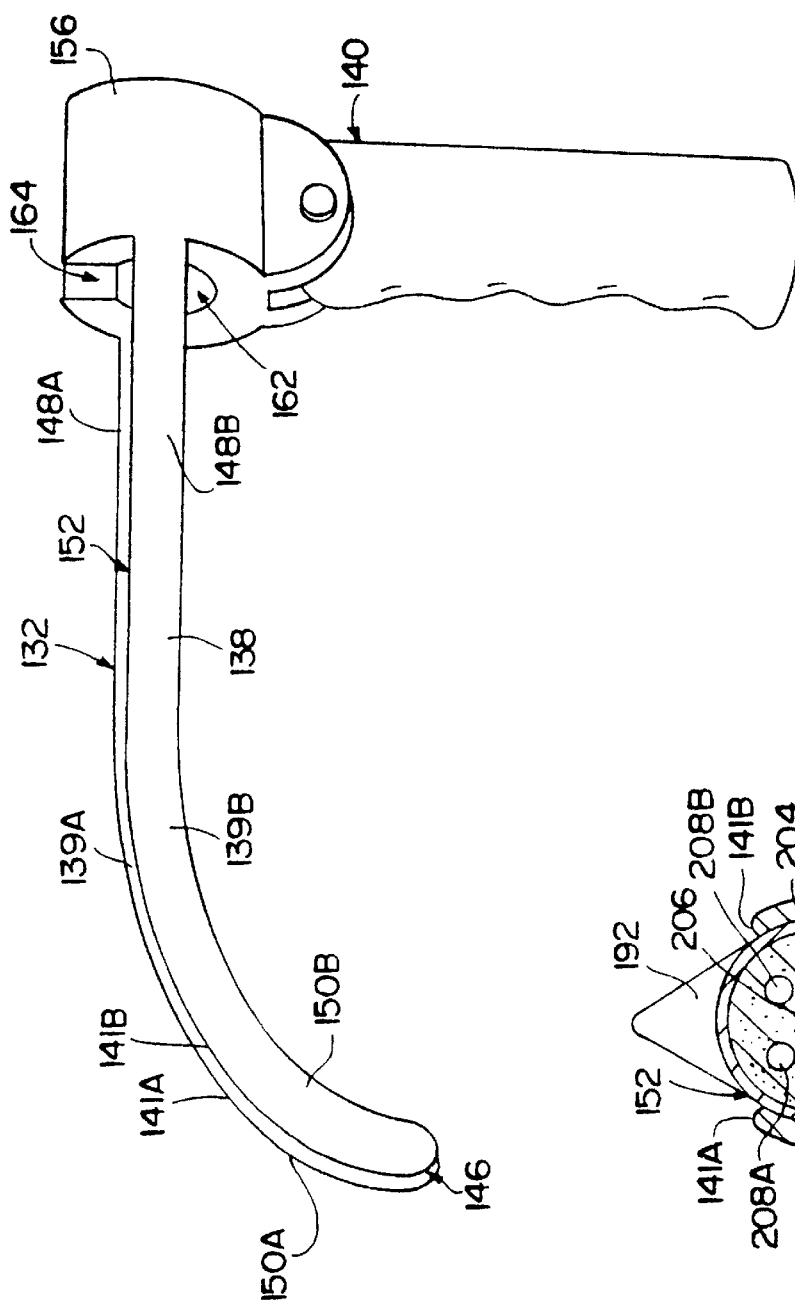
FIG. 9 is a perspective view of a modification of the blade assembly for the instruments according to the present invention.

A modification of the blade assembly for the instrument according to the present invention is illustrated in FIG. 9 at 132. Blade assembly 132 is similar to blade assembly 32, the primary difference between blade assembly 132 and blade assembly 32 being that blade 138 of blade assembly 132 includes one or more prongs 139. Blade assembly 132 includes blade 138 and blade handle 140 mounting blade 138, the blade handle 140 being similar to blade handle 40. Blade 138 is made up of one or more prongs 139, two opposed prongs 139A and 139B being shown for blade 138. Prongs 139A and 139B have straight proximal segments 148A and 148B and curved distal segments 150A and 150B, respectively. Prongs 139A and 139B are laterally spaced from one another 180° about a passage 146 and can be disposed parallel to one another as shown or non-parallel. Blade 138 includes a guide channel 152 formed by the space or gap between corresponding, opposed lateral edges 141A and 141B of the prongs 139A and 139B, respectively, for receiving a guide protrusion of the tubular member. The prongs 139 can have any desired configuration in cross-section including circular, partial circular, oval, square, rectangular and triangular configurations; however, it is preferable that the prongs have smooth or rounded edges or corners to prevent injury to anatomical tissue. The width or height of the prongs can vary from that shown such that the prongs can circumscribe more or less of the periphery of a member, such as a tubular member, positioned in passage 146. Collar 156 of handle 140 is similar to collar 56 and includes a track channel 162 aligned with passage 146 and a guide channel 164 aligned with guide channel 152. Collar 156 is different from collar 56 in that guide channels 152 and 164 face upwardly whereas guide channels 52 and 64 of collar 56 face a side of the instrument 30.

FIG. 10 illustrates in cross-section at 130 an alternative embodiment of an instrument according to the present invention utilizing the blade assembly 132. Instrument 130 is similar to instrument 30 and includes tube 172 disposed in passage 146 with a friction fit with guide tab 192 extending through guide channel 152 and probe 194 disposed in tube 172. Probe 194 is similar to probe 94 except that probe 194 is made as a length of light transmitting material such that the light transmitting channel 204 is formed by the light transmitting material of the probe itself, which does not include a sheath. Probe 194 has a centrally located image transmitting channel 206, delivery channels 208A and 208B and a suction channel 210.

Operation of instrument 130 in a procedure to introduce a tubular member in the body is similar to that previously described in that the blade assembly 132, the tubular member assembly 134 and the remote viewing assembly 136 are assembled as shown in FIG. 10 with the control section of the remote viewing assembly disposed at a proximal end of track channel 162. Blade 138 is utilized to retract and/or manipulate anatomical tissue and/or organ structure, and the probe 194 and/or the tube 172 are advanced individually or in conjunction relative to the blade 138 via the track system and/or the guide system to controllably advance the tube and/or the probe to a site in the body as confirmed by visualization at the eyepiece of the remote viewing device.

FIGS. 11A–11J illustrate in cross-section further embodiments of the instrument according to the present invention. FIG. 11A illustrates an instrument 230 including a blade 238 having an oval configuration in cross-section and a plurality of light transmitting optical fibers 309 disposed therein around a passage 246 within the optical fibers. Light transmitting fibers 309 are optically coupled with a light source (not shown) powered by a battery, such as battery 55 shown in FIG. 1, in the hand grip of the blade. Passage 246 has a circular configuration in cross-section to receive a tube 272 having a guide tab 292 disposed in guide channel 252 of the blade shown positioned along a longer side of the blade, it being understood that the position of the guide tab is preferably along a side of the instrument but can be variably positioned dependent upon user desires and convenience. A probe 294 is disposed in tube 272 and is similar to probe 194 including a light transmitting channel 304 and a central image transmitting channel 306; however, the delivery channels 308A and 308B and the suction channel 310 for probe 294 are arranged around the image transmitting channel 306 differently than the arrangement of the delivery and suction channels around the image transmitting channel of probe 194. It should be appreciated that the blade 238 can include an outer sheath 313 and an inner sheath 313' with fibers 309 disposed between the outer sheath and inner sheath as shown or without sheaths depending on the material of the blade.

FIG. 11B illustrates an instrument 330 including a blade 338 having a circular configuration in cross-section to define a circular passage 346 for receiving tube 372 having guide tab 392 disposed in guide channel 352 of the blade. A probe 394 is disposed in tube 372 and probe 394 is similar to probe 94 including a sheath 412, a light transmitting channel 404 formed by a plurality of optical fibers 409 within sheath 412, a central imaging transmitting channel 406, delivery channels 408A and 408B, suction channel 410 and working channel 411.

FIG. 11C illustrates an instrument 430 including a blade 438 having a triangular configuration in cross-section and a passage 446 therein having a circular configuration in cross-section to receive tube 472 having guide tab 492 disposed in guide channel 452 of the blade. A probe 494, similar to probe 94, is disposed in tube 472. Blade 438 is made of a light transmitting material to transmit light from a light source, such as a bulb, powered by a battery in the hand grip of the blade assembly.

In the instrument 530 of FIG. 11D, the distal end 544 of the blade 538, the distal end 576 of the tube 572 and the distal end 602 of the probe 594 are each angled or beveled, and are in alignment or substantially in alignment when the tube 572 is disposed within the blade 538 and the probe 594 is disposed within the tube 572. Probe 594 is similar to probe 394 and includes an outer sheath 612 with a plurality of light transmitting fibers 609 therein.

FIG. 11E illustrates an instrument 630 including a blade 638 having a U-shaped configuration in cross-section defining a passage 646 for receiving tube 672 having a guide tab 692 disposed in guide channel 652 of the blade. Blade 638 includes a pair of opposed, parallel, spaced legs 643 and a base 645 joining legs 643. Passage 646 is defined by the configuration of the legs 643 and base 645, and the guide channel 652 is defined by the space between opposing ends of legs 643 with the tube 672 being held between the legs 643 spaced from the base 645. A probe 694 is disposed in tube 672 and is similar to probe 394.

The instrument 730 illustrated in FIG. 11F is similar to the instrument 630 except that tube 772 of instrument 730 is disposed in passage 746 of U-shaped blade 738 to be held between legs 743 adjacent base 745. Accordingly, guide tab 792 can be lengthened as shown or legs 743 can be shortened to ensure protrusion of tab 792 through the guide channel 752.

FIG. 11G illustrates an instrument 830 including a blade 838 having a C-shaped configuration in cross-section defining a passage 846 for receiving tube 872 and a guide channel 852 defined by the space or gap between opposing ends of opposing curved sides 847A and 847B of the C-shaped blade for receiving guide tab 892 of tube 872. A probe 894 is disposed in tube 872 and is similar to probe 794.

The instrument 930 illustrated in FIG. 11H includes a blade 938 having a C-shaped configuration in cross-section similar to blade 838 except that blade 938 has a curved side 947A and a flattened side 947B. Tube 972 is received in passage 946 of blade 938 with a guide tab 992 of the tube in a guide channel 952 of the blade. A probe 994, similar to probe 94, is received in tube 972.

FIG. 11I illustrates an instrument 1030 including a blade 1038, similar to blade 138, made up of three spaced prongs 1039A, 1039B and 1039C arranged around a passage 1046 for receiving tube 1072 having probe 1094 therein. A guide channel 1052 for receiving guide tab 1092 of tube 1072 is defined by the gap or space between adjacent prongs 1039A and 1039B. Although prongs 1039 are shown not equally spaced about passage 1046, it will be appreciated that the prongs can be equally spaced or arranged in any desired manner.

The instrument 1130 illustrated in FIG. 11J is similar to instrument 230 except that the probe is part of the blade 1138 of instrument 1130. Blade 1138 has an oval configuration in cross-section and includes a plurality of light transmitting fibers 1209. A passage 1146 of blade 1138 receives tube 1172 with a tab 1192 of the tube extending through guide channel 1152. Image transmitting channel 1206, delivery channels 1208, suction channel 1210 and working channels 1211 are disposed in blade 1138 offset from tube 1172.

A modification of a tubular member assembly for the instruments according to the present invention is illustrated at 1234 in FIGS. 12 and 13 and includes a tube 1272 having a J-shaped distal segment 1250 with an angled distal end surface 1277 and a proximal end 1278 mounted to adapter 1274. A pair of spaced cuffs 1280 are disposed on tube 1272, the cuffs 1280 having peripheries in a non-distended or non-inflated state aligned or substantially in alignment with the periphery of tube 1272 such that the cuffs 1280 are essentially smooth continuations of tube 1272. A pair of opposed guide channels 1252 extend the length of the tubular member assembly 1234 at 180° spaced locations as shown in FIG. 13. Guide channels 1252 include recesses extending longitudinally the entire length of the tubular member assembly 1234 for cooperating with a guide protrusion of a blade assembly to form a guide system for guiding movement of tube 1272. Cuff distension tubes 1281A and 1281B communicating with valves 1283A and 1283B, such as stopcocks, are connected with tube 1272 for inflating cuffs 1280A and 1280B, respectively. Tubular member assembly 1234 is particularly advantageous in minimizing the space required for instruments according to the present invention due to the smooth continuation of cuffs 1280 with tube 1272 and in minimizing friction or pressure on cuffs 1280 when the tube 1272 is inserted in a blade.

FIG. 14 illustrates in cross-section an alternative embodiment of an instrument according to the present invention utilizing tubular member assembly 1234. Instrument 1230 illustrated in FIG. 14 includes a blade 1238 having a U-shaped configuration in cross-section defined by a pair of opposed, parallel, spaced legs 1243A and 1243B and a base 1245 joining legs 1243. Inwardly facing guide protrusions 1292 are disposed at ends of legs 1243A and 1243B for engaging guide channels 1252 of tube 1272 disposed in passage 1246. With the guide protrusions received in the guide channels, tube 1272 protrudes beyond legs 1243 such that the adapter 1274 of tubular member assembly 1234 is available for convenient grasping by an operator. Accordingly, guide channels 1252 and guide protrusions 1292 form a guide system for guiding longitudinal movement of tube 1272 along blade 1238 via cooperating structure of the tube and the blade. A probe can be disposed in tube 1272 with operation of instrument 1230 being similar to that already described.

FIG. 15 illustrates at 1330 another embodiment of an instrument according to the present invention. Instrument 1330 includes a tube 1372, and a blade 1338 made up of a single prong 1339 having a configuration in cross-section corresponding to a portion or arc of the circumference of tube 1372. A guide protrusion 1392 extends radially inwardly from prong 1339 and longitudinally along prong 1339 for engagement with a guide channel 1352 including a recess in tube 1372 to form a guide system for guiding longitudinal movement of tube 1372 along blade 1338.

FIGS. 16A–16C illustrate in cross-section various alternative configurations for the track system of the instruments according to the present invention. FIG. 16A illustrates a collar 1456 having a track channel 1464 therein with an oval configuration for cooperating with a control section 1496 having an oval configuration in cross-section. FIG. 16B illustrates a collar 1556 having a track channel 1564 therein with a diamond or parallelogram shaped configuration in cross-section for cooperating with a similarly configured control section 1596 with rotation of the control section 1596 being prevented due to the mating configuration of the control section 1596 with the track channel 1564. The track systems of FIGS. 16A and 16B prevent rotation or twisting movements of the remote viewing assembly. The collar 1656 of FIG. 16C has a track channel 1664 therein with a circular configuration in cross-section for receiving a control section 1696 having a circular cross-sectional configuration. The track system of FIG. 16C will permit the remote viewing device to rotate; and, where rotation of the remote viewing device is not desired, a stabilizing rod 1563 can be provided in the instrument as illustrated in FIG. 5. The stabilizing rod 1563 extends from the hand grip or some other portion of the remote viewing device in parallel with the control section to be slidably received in a longitudinally extending aperture or opening 1565 of the collar whereby rotation of the control section within the track channel will be prevented. The stabilizing rod can be releasably attached to the remote viewing assembly to allow removal of the stabilizing rod where rotation of the control section within the track channel is desired.

Other embodiments of instruments according to the present invention are illustrated in cross-section in FIGS. 17–21, which show various alternative arrangements for the blade assemblies, the tubular member assemblies and the remote viewing assemblies. FIG. 17 illustrates an instrument 1730 including a blade assembly and a tubular member assembly arranged within a remote viewing assembly. Probe 1794 for instrument 1730 can be provided with or without an outer sheath 1812 and includes a light transmitting channel 1804, an image transmitting channel 1806, delivery channels 1808A and 1808B, suction channel 1810 and operating channel 1811. A blade 1738 including three prongs 1739 is disposed in probe 1794, and a tube 1772 is disposed in operating channel 1811.

The instrument 1830 illustrated in FIG. 18 includes a tube 1872, a blade 1838 having a circular configuration in cross-section disposed in tube 1872 and a probe 1894 disposed in blade 1838 with the probe having a light transmitting channel 1904, a central image transmitting channel 1906, delivery channels 1908, suction channel 1910 and working channel 1911. Accordingly, in the instrument of FIG. 18 the remote viewing assembly is arranged within the blade assembly and the blade assembly is arranged in the tubular member assembly.

FIG. 19 illustrates an instrument 1930 wherein the tubular member assembly is arranged in the remote viewing assembly and the remote viewing assembly is arranged in the blade assembly. Instrument 1930 includes a blade 1938 having a circular configuration in cross-section, a probe 1994 disposed in blade 1938 and a tube 1972 disposed in a central operating channel 2011 of probe 1994. Probe 1994 has an image transmitting channel 2006, delivery channels 2008 and suction channel 2010 arranged around tube 1972 and a light transmitting channel 2004 in sheath 2012.

The instrument 2030 illustrated in FIG. 20 includes a blade assembly and a tubular member assembly arranged within a remote viewing assembly. The instrument 2030 includes a probe 2094 having a tube 2072 disposed in a working channel 2111 of the probe and a blade 2038 disposed in tube 2072. Probe 2094 has a light transmitting channel 2104, a central image transmitting channel 2106, two delivery channels 2108, suction channel 2110 and two working channels 2111. FIG. 21 illustrates an instrument 2130 having a tubular member assembly, a remote viewing assembly disposed within the tubular member assembly and a blade assembly disposed in the remote viewing assembly. Instrument 2130 includes probe 2194 disposed in tube 2172 and a blade including three prongs 2139 disposed in probe 2194.

Figure 22:
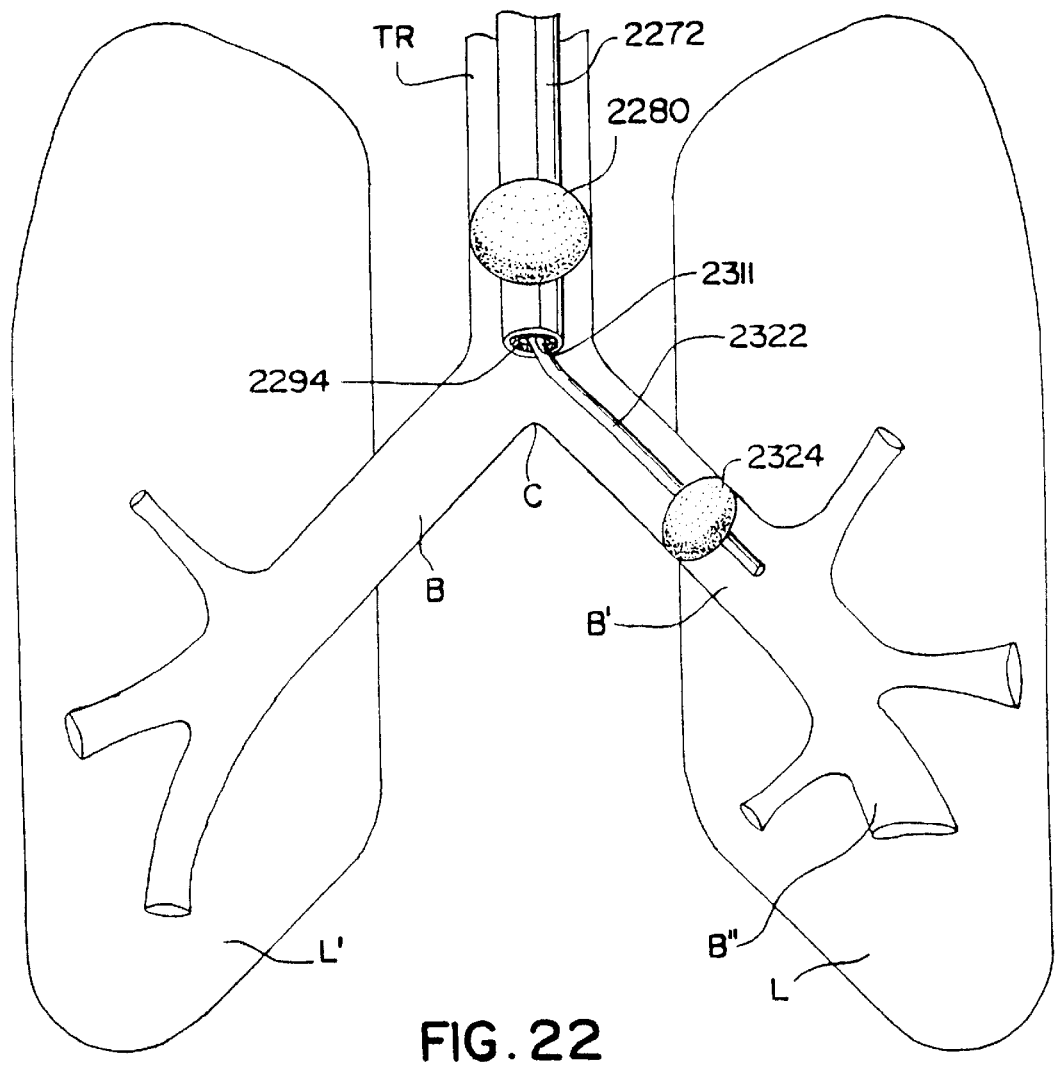
FIG. 22 illustrates a method of bronchial intubation according to the present invention.

A method of bronchial intubation utilizing the instrument of the present invention is illustrated in FIG. 22. The method of bronchial intubation according to the present invention includes the steps previously described for introducing an endotracheal tube in the trachea. As shown in FIG. 22, endotracheal tube 2272 of a tubular member assembly has been introduced in the trachea TR, and the cuff 2280 of the tube 2272 has been inflated to secure the tube 2272 in place in the trachea. The endotracheal tube 2272 is introduced in the trachea TR to a depth sufficient to position a distal end of the tube near the carina C, i.e. the junction of the trachea TR and the right and left bronchii B and B'. Proper introduction of the endotracheal tube 2272 in the trachea to the desired depth is confirmed with a remote viewing assembly having a probe 2294 disposed in tube 2272. A catheter 2322 having a cuff 2324 at a distal end thereof is introduced through a working or operating channel 2311 of the remote viewing device with the cuff in a non-inflated condition to position a distal end of the catheter 2322 in the left bronchus B'. The cuff 2324 is inflated with a cuff distension device similar to that previously described for the cuff of the endotracheal tube to secure the catheter in place in the bronchus B' allowing the left lung L to be collapsed in accordance with the medical procedure being performed. During the bronchial intubation procedure, ventilation or respiration can be maintained for the right lung L' via the delivery channel of the remote viewing device. Once the catheter 2322 is properly positioned and secured, the blade assembly, if not already withdrawn, and the remote viewing assembly can be withdrawn from the tubular member assembly leaving the tube 2272 and the catheter 2322 in place in the trachea and left bronchus, respectively. It should be appreciated that, depending on the medical procedure being performed, the catheter 2322 can be advanced further into the bronchus to position the distal end of the catheter in a bronchiole B", and the cuff 2324 inflated to secure the catheter in the bronchiole. Accordingly, the instruments of the present invention allow one or more tubular members to be introduced through the channels of the additional endoscope subsequent to introduction of a first tubular member.

Another embodiment of an instrument according to the present invention is illustrated at 2330 in FIG. 23, the instrument 2330 being particularly advantageous for use in vaginal and rectal procedures such as vagino-hysteroscopy, colposcopy, rectosigmoidoscopy and various other procedures for introducing tubular members in anatomical channels. The instrument 2330 includes a blade assembly 2332, a tubular member assembly 2334 and a remote viewing assembly 2336. The blade assembly 2332 includes a blade 2338 and a handle 2340 mounting a proximal end of blade 2338. Blade 2338 is made up of a single prong 2339 having a somewhat concave configuration in cross-section facing tube 2372 of tubular member assembly 2334 to define a guide passage 2352 as shown in FIG. 24. As shown in FIG. 24, prong 2339 is flexible and has an outer sheath 2413 with a plurality of light transmitting fibers 2409 disposed in sheath 2413. Left and right control wires 2351A and 2351B are disposed in sheath 2413 near lateral sides of the blade. Wires 2351A and 2351B extend longitudinally along blade 2338 and have distal ends connected to distal end 2344 of blade 2338, such as to sheath 2413 and/or fibers 2409, and proximal ends connected to left and right control wheels 2357A and 2357B mounted to handle 2340 as shown in FIGS. 24 and 25. Up and down control wires 2353A and 2353B are disposed in blade 2338 near the top and bottom of the blade, respectively. Wires 2353 extend longitudinally along the blade and have distal ends connected to distal end 2344 of the blade and proximal ends connected to up and down control wheels 2359A and 2359B mounted to handle 2340. Wires 2351 and 2353 are movable in blade 2338 in response to winding, stretching or pulling of the control wires or unwinding of the control wires by control wheels 2357 and 2359 to cause proximal or distal movement of the control wires, such as by winding or unwinding of the control wires around pins or axles of the control wheels. Movement of wires 2351 and 2353 by the control wheels results in a corresponding force being applied to blade 2338 due to connection of the distal ends of the control wires with the distal end of the blade. Accordingly, winding or pulling of left control wire 2351A will cause the distal end of blade 2338 to move to the left, looking proximally in FIG. 23, and pulling of right control wire 2351B by wheel 2357B will cause the distal end of the blade to move to the right. Pulling on the distal end of the blade by the up control wire 2353A in response to winding by wheel 2359A will cause the blade distal end to move upwardly, looking at FIG. 23, and pulling on the blade distal end by the down control wire 2353B in response to winding by wheel 2359B will cause the blade distal end to move downwardly. Accordingly, the distal end of blade 2338 is adjustable to selectively change the angular orientation of the distal end of the blade relative to the remainder of the blade. It will be appreciated that distal movement of the control wires, such as by unwinding of the control wires by the control wheels, will produce reverse movements of the blade distal end and that the control wheels can be provided with various mechanisms, such as releasable ratchet mechanisms, for locking the position of the control wheels to maintain various adjusted positions for the blade. As shown in FIG. 23 for control wheels 2357B and 2359B, a plurality of ratchet surfaces 2361 can be provided on the control wheels for engaging pivotable pawl 2367 on the handle 2340 to maintain the position of the control wheel and for allowing selective rotation of the control wheels. It should also be appreciated that the control wires can be manipulated in various ways in addition to the control wheels shown; and, where control wheels are utilized, all the left and right directional adjustments can be provided with a single control wheel and the up and down directional adjustments can be provided with a single wheel.

Blade handle 2340 includes a hand grip 2354 mounted to a collar 2356 which in turn mounts a proximal end of prong 2339. Collar 2356 has a track channel therein for slidably or movably receiving control section 2396 of remote viewing assembly 2336 to form a track system. Hand grip 2354 can be adjustably or rigidly mounted to collar 2356 and can include a battery for powering a light source to transmit light along fibers 2409 of blade 2338. Remote viewing assembly 2336 includes a flexible endoscope having control section 2396, a probe 2394 extending distally of control section 2396 and a handle 2400 mounting control section 2396. The control section 2396 terminates proximally at eyepieces 2398A and 2398B, the eyepiece 2398A being a normal eyepiece and the eyepiece 2398B being a microscopic or magnifying eyepiece such as found in the Hamou micro-colpohysteroscope manufactured by Storz. The probe 2394 has control wires therein connected to a distal end of the probe 2394 and to one or more control wheels, such as control wheels 2405 mounted on handle 2400 for controlling directional adjustment of the probe distal end to selectively change the angular orientation of the distal end of the probe 2394 relative to the remainder of the probe. One endoscope suitable for use in the instrument 2330 is the Olympus flexible endoscope. The tubular member assembly 2334 includes flexible tube 2372 terminating at angled distal end surface 2377 and an adapter 2374, similar to adapter 74, mounting a proximal end of tube 2372.

A method of operation for the instrument 2330 in introducing a tubular member in an anatomical cavity is illustrated in FIG. 23, the instrument 2330 being shown in a procedure for introducing the tubular member 2372 in the uterus. The blade assembly 2332, the tubular member assembly 2334 and the remote viewing assembly 2336 for instrument 2330 are assembled as shown in FIG. 23 with the probe 2394 disposed in tube 2372 with adapter 2374 in abutment with control section 2396 at which time the distal end 2402 of the probe and a distal end 2376 of the tube will be in alignment or substantially in alignment. With the instrument assembled as shown in FIG. 23, tube 2372 and probe 2394 will be disposed substantially parallel to blade 2338 with the curvature of the blade and the probe extending slightly downwardly. The guide tab 2392 of adapter 2374 will be in engagement with a curved surface of blade 2338 to form a guide system for guiding movement of tube 2372 along the blade. Adapter 2374 has a second opposing guide tab 2392' disposed opposite guide tab 2392 for being manually grasped to move tube 2372 back and forth along the blade.

The instrument 2330 is introduced through the vagina to position blade 2338 along a posterior vaginal wall W or surface of the vaginal canal V. The blade 2338 is utilized to retract the posterior vaginal wall W by applying downward or posterior pressure or force with the blade 2338 upon the posterior vaginal wall W. Control wires 2351 and 2353 are manipulated via the control wheels to adjust the position, orientation or angular direction of the distal end of the blade 2338 upwardly, downwardly, to the left or to the right relative to the remainder of the blade. With the blade held in place against the vaginal wall, control wheels 2405 are utilized to selectively adjust the direction, orientation or position of the probe distal end 2402 relative to the remainder of the probe 2394. Since the probe 2394 is disposed in tube 2372, the distal end of the tube 2372 is moved by the distal end of the probe 2394 such that changing the angular orientation of the distal end of probe 2349 relative to the remainder of the probe correspondingly changes the angular orientation of the distal end of the tube 2372 relative to the remainder of the tube. FIG. 23 shows in dotted lines the distal end 2402 of probe 2394 moved upwardly substantially 180° from its initial position to position the distal end 2376 of tube 2372 in alignment with the cervical opening or os O of the uterus U at which time end surface 2377 of tube 2372 will be optimally positioned transversely to enter the cervical os. The probe 2394 and the tube 2372 can be advanced forwardly or distally via sliding movement of the control section 2396 in the track channel to introduce the distal end 2376 of the tube 2372 and the distal end 2402 of the probe in the uterus U. The eyepieces 2398 are utilized to confirm proper introduction of tube 2372 in the uterus with eyepiece 2398B allowing microscopic examination of tissue and organ structure. Where it is desired to introduce tube 2372 further into the uterus, the guide tab 2392' is grasped and the tube 2372 is moved distally along the blade 2338 with the guide system controlling distal movement of the tube. One or more cuffs 2380A and 2380B of tube 2372 can be inflated to permit manipulation of tissue and/or prevent backing out of tube 2372 from the uterus as well as to facilitate or perform various other procedures such as separating adhering tissue (lysis of adhesion), the cuffs being shown inflated in dotted lines in FIG. 23. Conduits 2418 of the endoscope are utilized to introduce fluids or other substances or instruments or to apply suction via the channels of the endoscope. Once tube 2372 has been properly introduced and positioned in the uterus, the blade assembly and the remote viewing assembly can be withdrawn from the tubular member assembly leaving the tube in place in the body and various instruments can be inserted through tube 2372 to perform various medical procedures. It should be appreciated that the instrument can be designed in many various ways to change the direction of or position the distal end of the blade, the probe, and/or the tube; and, accordingly, with the instruments of the present invention, the blade, the tubular member and/or the remote viewing device can be adjustable.

Figure 26:
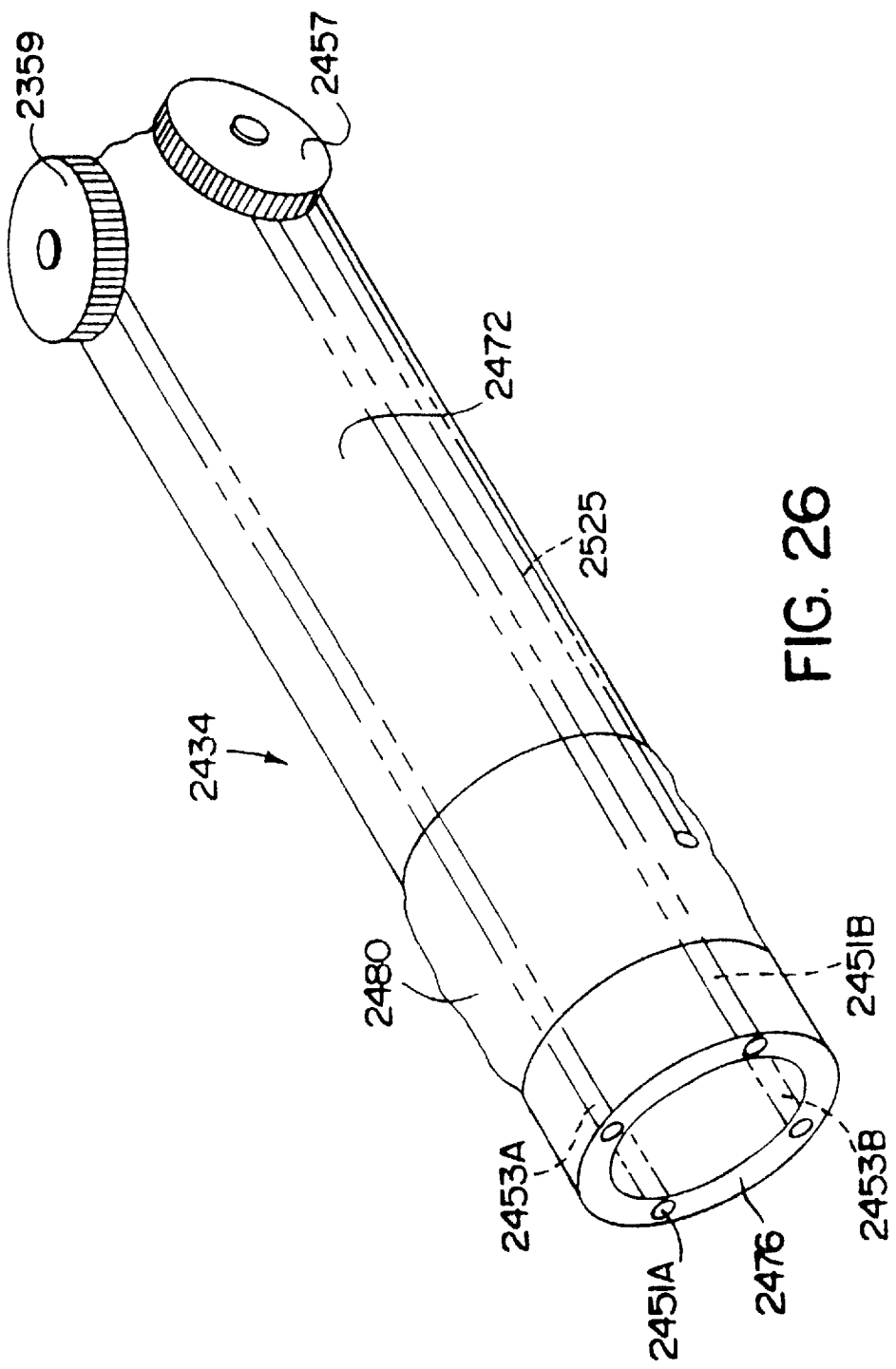
FIG. 26 is a broken perspective view of a modification of a tubular member assembly for use with the instruments of the present invention.

FIG. 26 illustrates at 2434 a modification of a tubular member assembly for use with the instruments of the present invention. Tubular member assembly 2434 includes tube 2472 having an inflatable cuff 2480 for inflation by a cuff distension device communicating with a channel 2525 in the wall of the tube in turn communicating with cuff 2480 as previously described for tube 72. Tube 2472 has left and right control wires 2451A and 2451B and up and down control wires 2453A and 2453B disposed in the wall of the tube. The control wires 2451 have distal ends connected to tube 2472 and proximal ends connected to left and right control wheel 2457 for controlling left and right or lateral movements of the tube distal end 2476. The control wires 2453 have distal ends connected to tube 2472 and proximal ends connected to an up and down control wheel 2359 for controlling upward and downward movement of the tube distal end 2476 as previously described for blade 2338 such that tube 2472 is selectively adjustable to optimally position the distal end of the tube.

With the instruments of the present invention, normal or straightforward endotracheal intubation as well as difficult endotracheal intubation can be performed with a single instrument by a wide range of medical personnel having various levels of skill. By providing one instrument for use in all endotracheal intubations, the present invention eliminates or greatly minimizes the problems of difficult endotracheal intubations and, in particular, unanticipated difficult endotracheal intubations, and enhances the safety and efficacy of all intubations. Controlled distal movement of the probe and endotracheal tube provided by the track system allows the endotracheal tube and probe to be accurately and controllably introduced in the trachea through the exposed glottis as facilitated by manipulation of anatomical tissue with the blade. Proper introduction of the tube in the trachea is able to be visually confirmed at the eyepiece of the remote viewing device by observing the anatomical characteristics or landmarks of the trachea; and, if the tube has been inadvertently introduced in the esophagus, the anatomical characteristics or landmarks of the esophagus will be recognized at the eyepiece allowing the tube to be quickly withdrawn from the esophagus and properly introduced in the trachea. Distal movement of the tube provided by the guide system further ensures introduction of the tube in the trachea as well as introduction in the trachea to the desired depth or distance to prevent the tube from being introduced too far or not far enough. Accordingly, unrecognized introduction of an endotracheal tube too far into the trachea such that the cuff of the tube inadvertently enters the bronchus and results in adverse consequences when inflated can be avoided. The track system and guide system can be designed to prevent undesired rotation or lateral movement of the remote viewing device and the tube or to allow rotation and to ensure optimal orientation of a distal end of the tube.

The arrangements of the blade assembly, the tubular member assembly and the remote viewing assembly in the instruments of the present invention permit longitudinal movement of the tubular member assembly, the remote viewing assembly and/or the blade assembly relative to each other to allow use in various procedures; and, when the blade assembly is disposed within the tubular member assembly or the remote viewing assembly, the blade assembly can be used as a stylet prior to being moved distally out of the distal end of the instrument for use as a blade to manipulate or retract tissue. The arrangements also minimize the space required for the instrument to facilitate passage through relatively narrow body channels or openings, to minimize or eliminate interference with visualization by structure of the instruments, and to define a smooth outer peripheral surface or shape to prevent damage to anatomical tissue or organ structure. With the use of a magnifying or microscopic eyepiece, anatomical tissue and/or organ structure can be examined incident to tube introducing procedures to allow identification of diseases and abnormalities, such as cancerous and pre-cancerous areas. When used in endotracheal intubation, the instruments of the present invention permit early diagnosis of cancers and other abnormalities, such as cancer of the vocal cords or larynx, incidental to endotracheal intubation. With the use of a charge coupled device, intubation procedures as well as specific tissue and/or organ structure can be observed on a television monitor and videographed for recordation. The instruments of the present invention can be utilized with a photographic device such as a camera attached to the normal and/or magnifying eyepieces allowing a photographic image to be taken of specific areas for subsequent examination, one suitable device being the Pentax VV200 System. The instruments according to the present invention are simplified in construction and operation and are suitable for use in emergency situations for enhanced success in lifesaving efforts and other medical procedures.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of introducing a tubular member at a site in the body utilizing an instrument for introducing a tubular member at a site in the body comprising the steps of
    inserting a blade of a blade assembly of the instrument in the body;
    retracting anatomical tissue with a distal end of the blade to expose the site in the body;
    moving a tubular member and a remote viewing device of the instrument distally relative to and along the blade toward the site in the body while the distal end of the blade retracts the anatomical tissue;
    guiding distal movement of the tubular member and the remote viewing device along the blade such that the tubular member and the remote viewing device are guided toward the site in the body;
    positioning a distal end of the tubular member and a distal end of the remote viewing device at the site in the body; and
    visualizing positioning of the distal end of the tubular member at the site in the body with the remote viewing device from a location external of the body.

2. A method as recited in claim 1 and further including, subsequent to said step of positioning, the step of advancing the distal end of the tubular member further distally relative to the blade and the remote viewing device.

3. A method as recited in claim 2 wherein said step of moving includes moving the tubular member and the remote viewing device within the same passage of the blade.

4. A method as recited in claim 1 wherein said step of moving includes moving the tubular member and the remote viewing device within the blade.

5. A method as recited in claim 4 wherein said step of advancing includes guiding distal advancement of the tubular member along the blade.

6. A method as recited in claim 1 wherein said step of positioning includes selectively changing the angular orientation of the distal end of the tubular member relative to the remainder of the tubular member.

7. A method as recited in claim 6 wherein the remote viewing device is disposed within the tubular member and said step of selectively changing includes selectively changing the angular orientation of the distal end of the remote viewing device relative to the remainder of the remote viewing device to correspondingly change the angular orientation of the distal end of the tubular member.

8. A method as recited in claim 7 wherein said step of selectively changing the angular orientation of the distal end of the remote viewing device includes moving the distal end of the remote viewing device laterally relative to the remainder of the remote viewing device.

9. A method as recited in claim 7 wherein said step of selectively changing the angular orientation of the distal end of the remote viewing device includes moving the distal end of the remote viewing device vertically relative to the remainder of the remote viewing device.

10. A method as recited in claim 7 wherein said step of selectively changing the angular orientation of the distal end of the remote viewing device includes moving the distal end of the remote viewing device laterally and vertically relative to the remainder of the remote viewing device.

11. A method as recited in claim 1 wherein said step of retracting includes selectively changing the angular orientation of the distal end of the blade relative to the remainder of the blade.

12. A method as recited in claim 11 wherein said step of selectively changing the angular orientation of the distal end of the blade includes moving the distal end of the blade laterally relative to the remainder of the blade.

13. A method as recited in claim 11 wherein said step of selectively changing the angular orientation of the distal end of the blade includes moving the distal end of the blade vertically relative to the remainder of the blade.

14. A method as recited in claim 11 wherein said step of selectively changing the angular orientation of the distal end of the blade includes moving the distal end of the blade laterally and vertically relative to the remainder of the blade.

15. A method as recited in claim 1 wherein said step of visualizing includes visualizing positioning of the distal end of the tubular member at the site in the body with an eyepiece of the remote viewing device.

16. A method as recited in claim 1 wherein said step of visualizing includes illuminating the site in the body with the remote viewing device.

17. A method as recited in claim 1 wherein said step of visualizing includes illuminating the site in the body with the blade.

18. A method as recited in claim 1 wherein said step of visualizing includes magnifying an image of anatomical tissue at the site in the body and observing the magnified image with the remote viewing device, from the location external of the body, to detect abnormalities in the anatomical tissue.

19. A method as recited in claim 18 wherein said step of observing includes observing the magnified image with an eyepiece of the remote viewing device.

20. A method as recited in claim 1 and further including, after said step of visualizing, the step of withdrawing the blade assembly and the remote viewing device from the site in the body leaving the tubular member at the site in the body.

21. A method as recited in claim 1 and further including, subsequent to said step of visualizing, the step of introducing another tubular member at the site in the body through a channel of the remote viewing device.

22. A method as recited in claim 1 and further including, subsequent to said step of visualizing, the step of introducing a tube at the site in the body through the tubular member.

23. A method as recited in claim 22 wherein said step of introducing a tube includes introducing the tube through a channel of the remote viewing device disposed in the tubular member.

24. A method as recited in claim 1 and further including the step of introducing an instrument at the site in the body through a channel of the remote viewing device.

25. A method as recited in claim 1 and further including the step of introducing a fluid at the site in the body through a channel of the remote viewing device.

26. A method as recited in claim 25 wherein said step of introducing a fluid includes introducing a gas through the channel of the remote viewing device.

27. A method as recited in claim 25 wherein said step of introducing a fluid includes introducing a medicament through the channel of the remote viewing device.

28. A method as recited in claim 1 and further including the step of withdrawing a fluid from the site in the body through a channel of the remote viewing device.

29. A method as recited in claim 1 and further including the step of introducing an instrument at the site in the body through the tubular member.

30. A method as recited in claim 1 wherein said step of inserting includes inserting the blade in the body with the tubular member and the remote viewing device concentrically arranged within a passage of the blade.

31. A method as recited in claim 30 wherein said step of inserting includes inserting the blade in the body with the remote viewing device disposed within the tubular member.

32. A method as recited in claim 1 wherein said step of inserting includes inserting the blade in the vagina and said step of retracting includes retracting the posterior vaginal wall.

33. A method as recited in claim 32 wherein said step of retracting includes selectively changing the angular orientation of the distal end of the blade relative to the remainder of the blade.

34. A method as recited in claim 32 and further including, prior to said step of moving, the step of aligning the distal end of the tubular member with the cervical os.

35. A method as recited in claim 34 wherein said step of aligning includes selectively changing the angular orientation of the distal end of the tubular member relative to the remainder of the tubular member to align the distal end of the tubular member with the cervical os.

36. A method as recited in claim 35 wherein said step of inserting includes inserting the blade in the body with the tubular member disposed in a passage of the blade and the remote viewing device disposed in the tubular member and said step of selectively changing includes selectively changing the angular orientation of the distal end of the remote viewing device relative to the remainder of the remote viewing device to correspondingly change the angular orientation of the distal end of the tubular member.

37. A method as recited in claim 34 wherein said step of moving includes moving the tubular member and the remote viewing device through the cervical os.

38. A method as recited in claim 37 wherein said step of positioning includes positioning the distal end of the tubular member and the distal end of the remote viewing device in the uterus.

39. A method as recited in claim 38 and further including, subsequent to said step of visualizing, the step of distending a cuff on the distal end of the tubular member.

40. A method as recited in claim 39 and further including, subsequent to said step of distending, the step of manipulating anatomical tissue with the cuff.

41. A method as recited in claim 40 wherein said step of manipulating includes performing lysis of adhesion.

42. A method as recited in claim 39 and further including, subsequent to said step of distending, the step of preventing backing out of the tubular member from the uterus with the cuff.

* * * * *